United States Patent [19]

Matsuda et al.

[11] Patent Number: 4,966,853
[45] Date of Patent: Oct. 30, 1990

[54] CELL CULTURING APPARATUS

[75] Inventors: Shoichi Matsuda; Akira Suzuki, both of Tokyo; Tatsuo Kaise, Yokosuka, all of Japan

[73] Assignee: Kirin Beer Kabushiki Kaisha, Tokyo, Japan

[21] Appl. No.: 158,663

[22] Filed: Feb. 22, 1988

[30] Foreign Application Priority Data

Jul. 20, 1987 [JP] Japan .................................. 62-180386
Jan. 22, 1988 [JP] Japan ............................. 63-60190[U]

[51] Int. Cl.⁵ .......................................... C12M 3/00
[52] U.S. Cl. .................................... 435/284; 422/63; 435/296; 435/300; 435/809
[58] Field of Search ............................ 422/63, 64, 65; 435/284, 296, 300, 312, 809

[56] References Cited

U.S. PATENT DOCUMENTS

| | | | |
|---|---|---|---|
| 3,618,734 | 11/1971 | Khan | 435/809 X |
| 4,039,287 | 8/1977 | Moran | 422/65 |
| 4,090,921 | 5/1978 | Sawanura et al. | 435/284 |
| 4,160,699 | 7/1979 | Sogi et al. | 435/287 |
| 4,250,266 | 2/1981 | Wade | 435/289 |
| 4,528,159 | 7/1985 | Liston | 422/65 |
| 4,609,017 | 9/1986 | Coulter et al. | 422/65 X |
| 4,727,033 | 2/1988 | Hijikata et al. | 436/69 |
| 4,785,407 | 11/1988 | Sakagami | 422/64 X |
| 4,797,258 | 1/1989 | Mochida | 422/65 |
| 4,800,164 | 1/1989 | Bisconte | 435/313 X |

FOREIGN PATENT DOCUMENTS 0787632 6/1968 Canada .............................. 422/65

*Primary Examiner*—Robert J. Warden
*Assistant Examiner*—Rebekah A. Griffith
*Attorney, Agent, or Firm*—Ladas & Parry

[57] ABSTRACT

A cell culturing apparatus and a cell culturing method are disclosed. A rack supporting apparatus includes a loop tracking and a plurality of culturing racks connected one after another in series. Each of the culturing racks accommodates culturing containers therein for cell culturing during their travel on the loop tracking. Each of the racks is accessible, through conveyors, to a container handling station where culture medium is filled in the culturing containers and cell inoculation is carried out. The culturing containers processed in the container handling station are automatically accommodated into the rack by an infeed station for starting cell culturing, and the culturing containers in which cell culturing have been performed in the rack are automatically discharged therefrom by a discharge station.

14 Claims, 25 Drawing Sheets

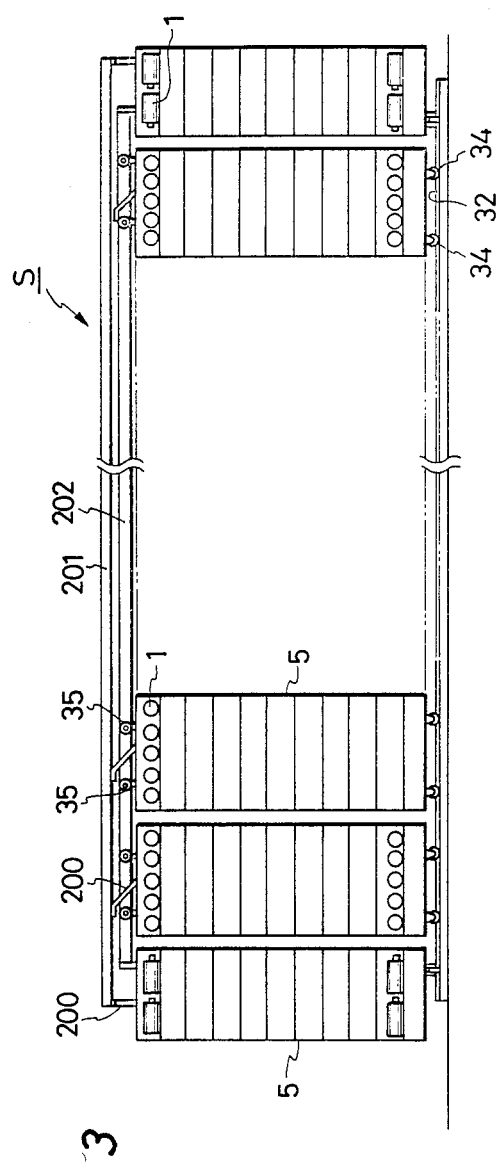
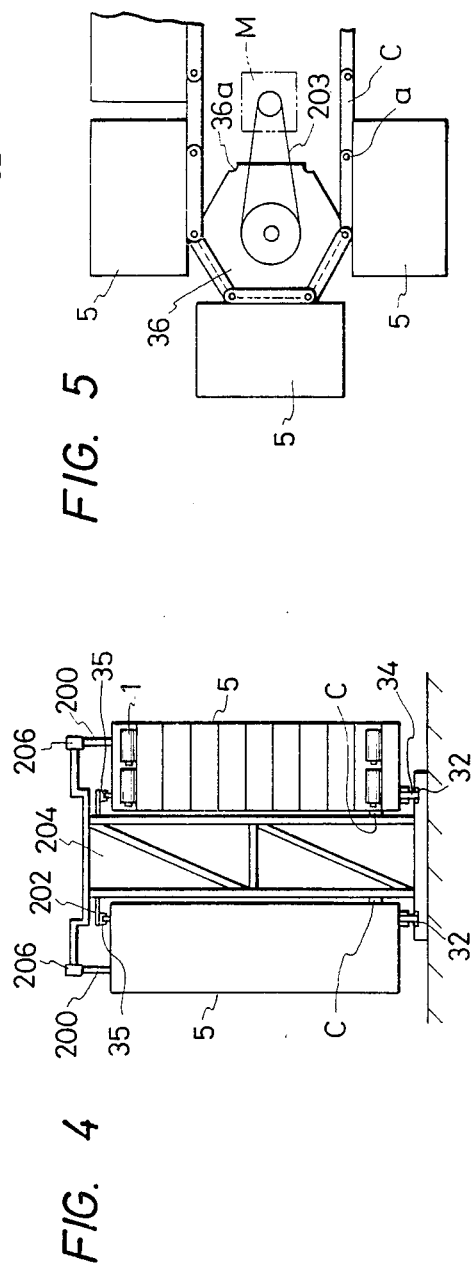
FIG. 3
FIG. 5
FIG. 4

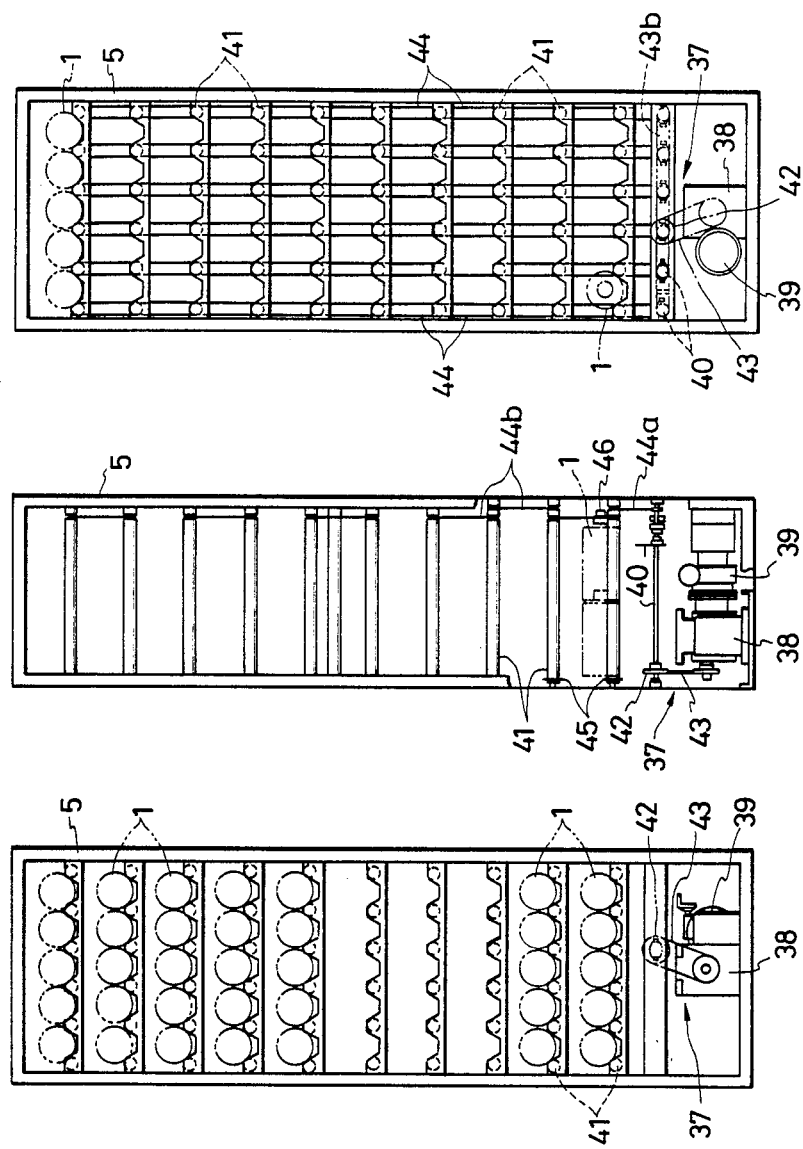

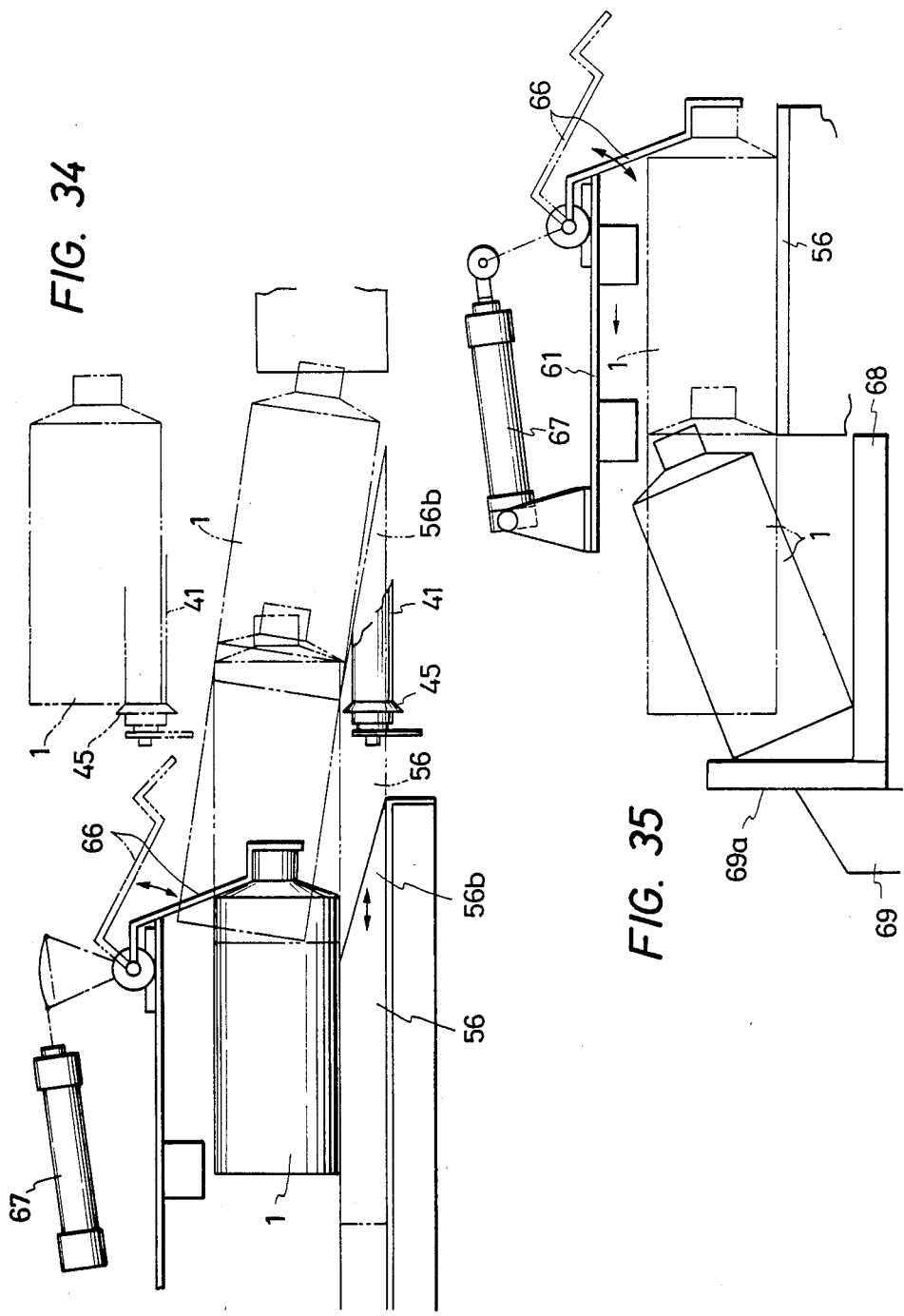

|          | CAP OPEN | SUCKING 1 | FILLING 1 | ROTATION | SUCKING 2 | FILLING 2 | CAPPING |
|----------|----------|-----------|-----------|----------|-----------|-----------|---------|
| 1st STEP | ○ | → | ○ | → | → | ○ | ○ |
| 2nd STEP | ○ | ○ | ○ | ○ | ○ | ○ | ○ |
| 3rd STEP | ○ | → | → | → | ○ | ○ | ○ |
| 4th STEP | ○ | ○ | → | → | → | → | ○ |

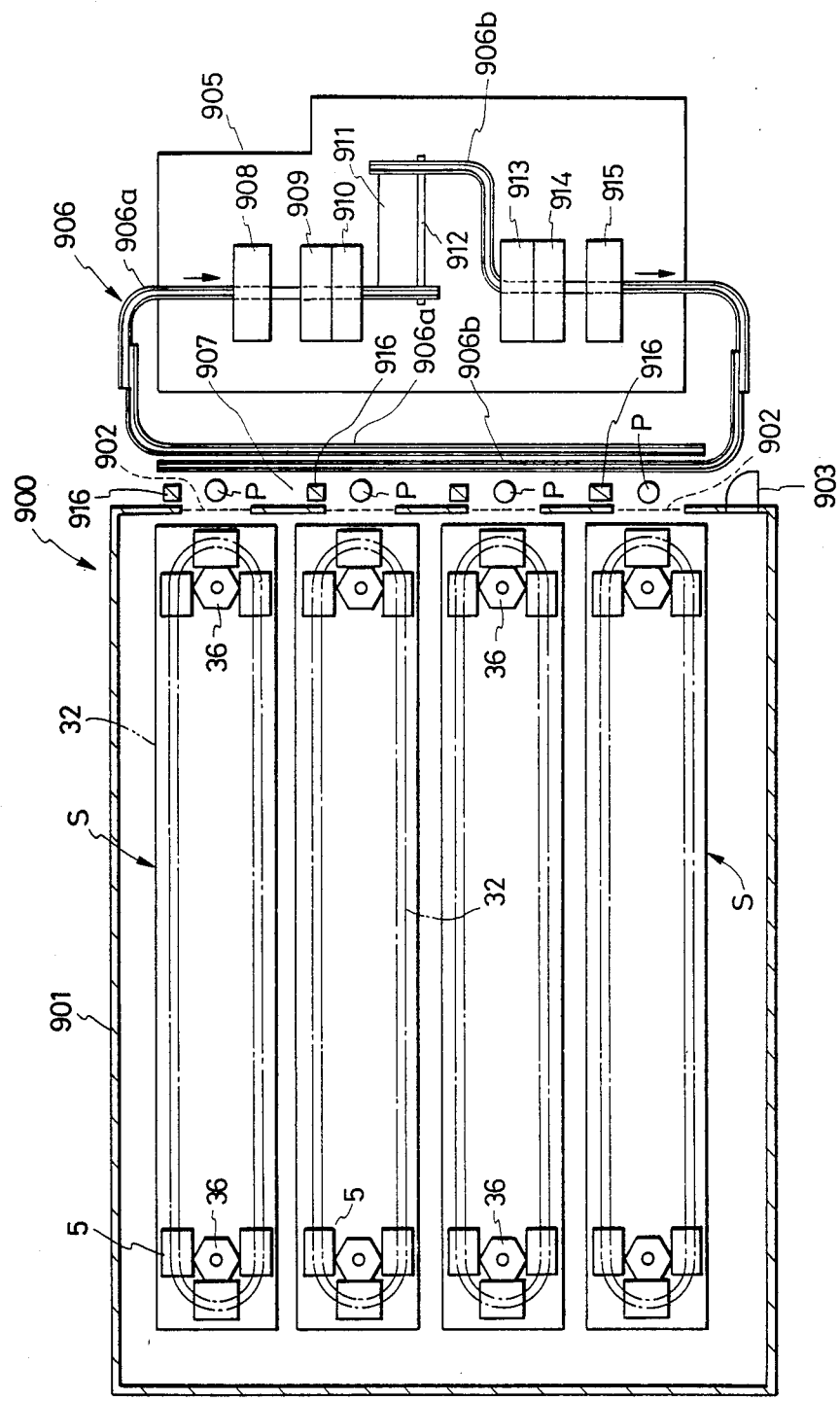

CELL CULTURING APPARATUS

BACKGROUND OF THE INVENTION

The present invention relates to a cell culturing apparatus and cell culturing method for culturing zooblast or animal cells, microorganism and fungus, and plant structural pieces.

Generally, for the above cell cultivations, culture medium is supplied to a culturing container such as a roller bottle and a tray etc., and cells are inoculated thereon. Thereafter, such culturing container is placed in a culturing rack at a constant temperature for a predetermined period of time for promoting the cell cultivation. Upon completion of the cultivation, the culturing container is discharged from the culturing rack, for collecting cultured cells and their metabolic substance.

A system for automatically handling the culturing containers has been proposed in commonly assigned U.S. application Ser. No. 099,341 filed on Sept. 21, 1987 now U.S. Pat. No. 4,761,936 or European Patent Application No. 87113905.1 filed Sept. 23, 1987. In this handling system, the filling and exchange of culture medium and cells relative to the culturing containers are automatically performed.

In this proposal, automatic filling of the cells and culture medium into the culturing containers and automatic discharge of these from the containers are attainable, and therefore, container handling efficiency can be improved. However, after the container handling operation, it is necessary to transfer the processed containers into the culturing racks, and prior to the container handling operation, it is necessary to transfer the containers after culturing from the racks to the handling system. For this, personnel manually insert the containers into the racks for culturing, and manually discharge the containers from the rack after culturing and manually insert the same into the handling system.

In this case, since an interior space of a culturing chamber has a temperature about 37° C. which temperature is higher than bodily temperature, such manual labors may cause pain to the personnel. As a result, such manual operations may reduce resultant container handling and transferring efficiency, and overall processes may become costly. Further, there is a fear by the individual personnel of contamination by various bacilli if they work in the culturing chamber for a long time. Therefore, there exists a large demand for conducting the entire processing automatically so preventing personnel from entering the culturing chamber.

SUMMARY OF THE INVENTION

It is therefore an object of the present invention to overcome the above-described drawbacks and disadvantages and to provide an improved cell culturing apparatus.

Another object of this invention is to provide such apparatus capable of performing the efficient processing of culturing containers while preventing personnel from contamination with bacilli.

According to one aspect of the invention, there is provided an improved cell culturing apparatus which uses culturing containers containing therein cells and culture medium for cell culturing. The apparatus comprises: a rack supporting apparatus comprising a loop track, and a plurality of culturing racks adapted to travel on said loop track, each of the racks accomodating therein a plurality of culturing containers for cell culturing during their travel on the loop track; an infeed station disposed at a position alongside the loop track for automatically supplying the culturing containers into the culturing racks; and, a discharge station disposed at a position alongside the loop track for automatically discharging the culturing containers which have been subjected to culturing from the culturing racks and for feeding the culturing containers for a subsequent process.

According to another aspect of the invention, there is provided an improved cell culturing apparatus for culturing cells mixed with culture medium contained in culturing containers. The apparatus comprises a plurality of culturing racks one after another in a series for their travel on a loop track, each of the culturing racks being adapted to accomodate therein a plurality of the culturing containers; aligning the plurality of culturing containers side by side in their upstanding postures on an infeed conveyor, the aligning being performed along the loop track at a container infeeding position; changing orientation of the plurality of culturing containers from their upstanding postures to horizontally lying postures; vertically moving horizontally oriented culturing containers to a position corresponding to a vertical height of one stage of the culturing racks; pushing the plurality of lying containers in horizontal direction for accomodating the containers in the culturing rack; leaving the culturing containers in the culturing rack for a predetermined period of time for cell culturing in the rack; pushing in horizontal direction the plurality of containers on the stage of the rack toward outside the rack at a container discharge position; receiving the horizontally oriented culturing containers and vertically moving the latter to a predetermined position; changing orientation of the plurality of culturing container from their horizontally lying posture to their upstanding postures at the predetermined position; and transferring the upstanding culturing containers to a discharge conveyor for subsequent step.

These and other objects of this invention will become more apparent from the detailed description of particular embodiments with reference to accompanying drawings.

BRIEF DESCRIPTION OF THE DRAWINGS

FIG. 3 is a side elevational view showing a rack supporting apparatus of this invention;

FIG. 4 is a front elevational view showing the rack supporting apparatus shown in FIG. 3;

FIG. 5 is a plan view showing a drive means for driving the culturing racks;

FIG. 21 is a front elevational view particularly showing a mechanism for driving rollers in the rack; and, FIG. 22 is a side elevational view of the rack and the roller driving mechanism those shown in FIG. 21;

FIG. 23 is a front elevational view showing the culturing rack in which a power transmission mechanism of the roller driving mechanism is delineated;

FIG. 34 is an explanatory illustration showing a transfer of the culturing container from the culturing rack to the discharge lifter;

FIG. 35 is an explanatory illustration showing a transfer of the culturing container from the discharge lifter to an upstanding mechanism;

FIG. 46 is a plan view showing a cell culturing apparatus according to another embodiment of this invention; and, FIG. 47 is a partial cross-sectional view taken from FIG. 46.

DETAILED DESCRIPTION OF THE PREFERRED EMBODIMENTS

One embodiment according to this invention will now be described with reference to accompanying drawings.

General Arrangement

Figure 1:
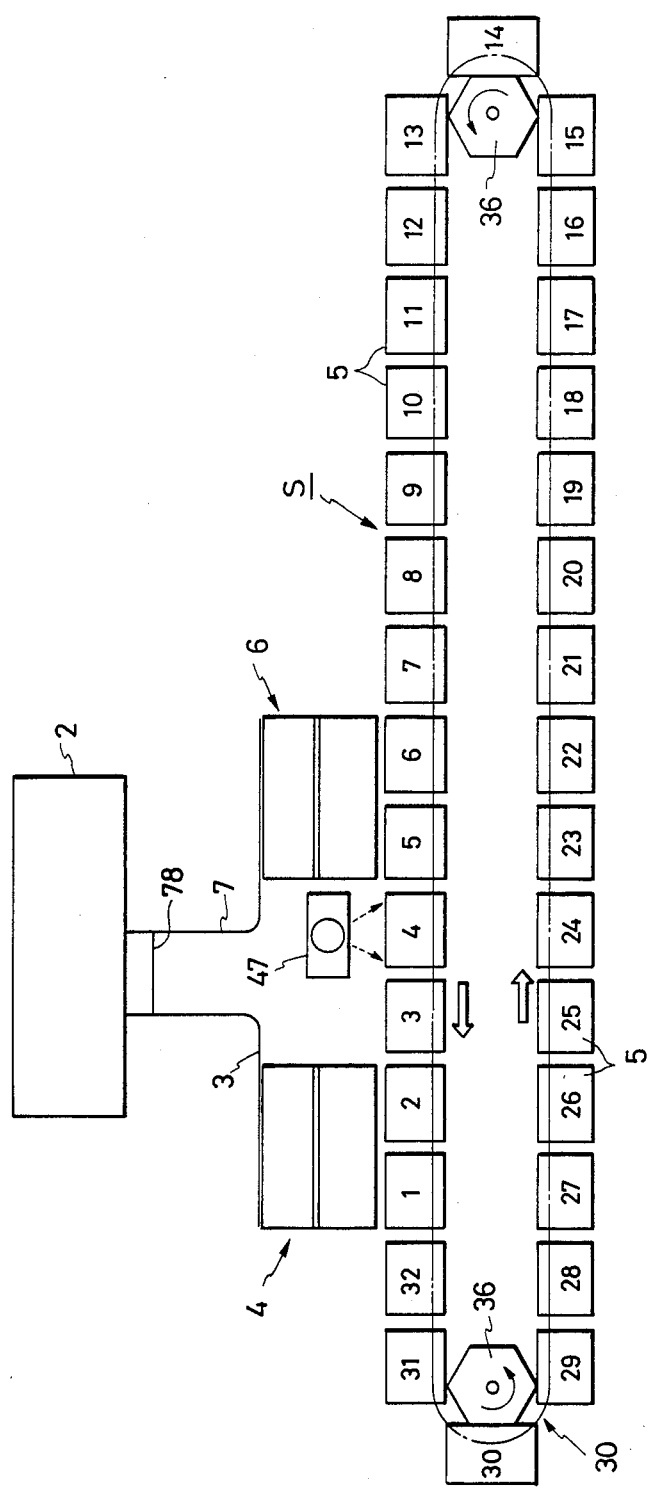
FIG. 1 is a schematic plan view showing a cell culturing apparatus according to one embodiment of this invention.
Figure 2:
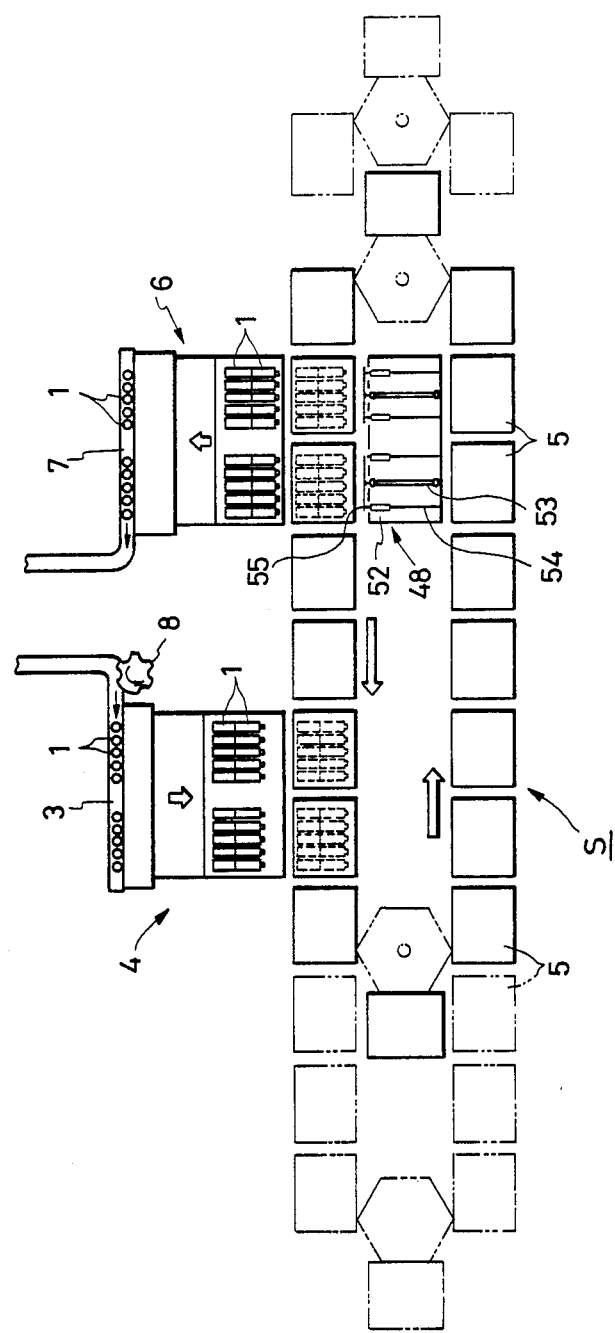
FIG. 2 is a schematic plan view of the sell culturing apparatus particularly showing container infeed and discharge stations according to one embodiment of this invention.

A cell culturing apparatus according to the embodiment shown in FIGS. 1 thru 2 is adapted to perform cell culturing and exchange with respect to rotary cylinder type cell culturing containers (roller bottles) in which culture medium and cells are contained. The cell culturing apparatus generally includes a handling station 2, an infeed station 4, a rack supporting apparatus S including rotary type culturing racks 5, and a discharge station 6. In the handling station, filling of culture medium into the roller bottles, cell inoculation, and rinsing of the roller bottles are performed. The roller bottles containing therein the cells and culture medium are automatically supplied from the handling station 2 to the infeed station 4 by an infeed conveyor 3, and the culturing containers 1 are transferred from the infeed station to the rotary culturing racks 5 which are movable on a loop path of the rack supporting apparatus S. During the travel of the racks, cell culturing is promoted in the roller bottles 1. The culturing containers 1 are then automatically discharged from the culturing racks 5 to the discharge station 2 and are transferred to the handling station 2 by a discharging conveyor 7. In the handling station 2, the cultured cells are removed from the containers 1, and the bottles are subjected to insertion of new cells and culture medium.

Figure 7:
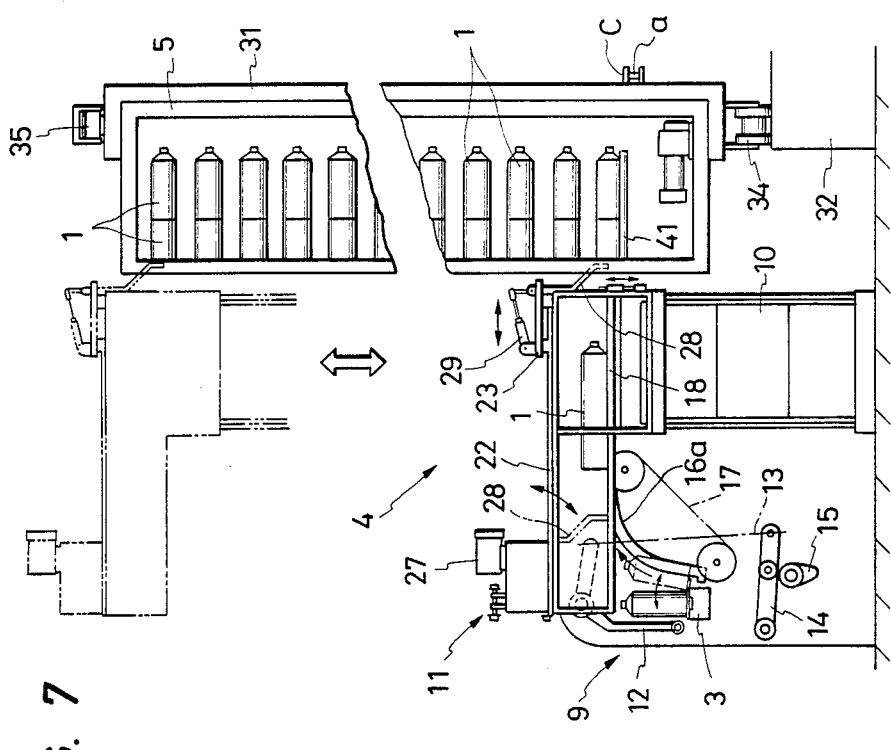
FIG. 7 is a side elevational view of the infeed station; and, FIG. 8 is an enlarged side elevational view showing the infeed station.
Figure 6:
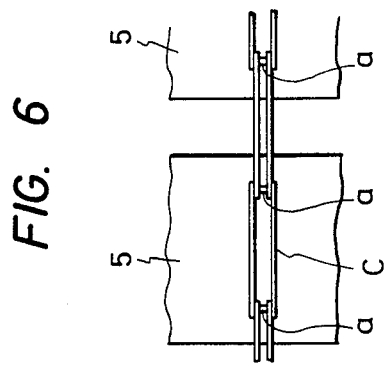
FIG. 6 is an illustration showing the relationship between the culturing racks and chains fixedly secured thereto.

The rack supporting apparatus S connects a plurality of racks 5 one after another in the loop tracking path. As shown in FIG. 4, a base frame 204 vertically extends at longitudinal ends of the loop path and hexagonal sprockets 36, 36 are disposed at the longitudinal ends. At the upper lateral sides of the base frame 204, a guide rail 202 is installed. Each of the racks 5 is provided with a roller 35 at its upper portion thereof which roller 35 is engageable with the guide rail 202. Further, a contact rod 200 extends from each upper surface of the racks 5. The contact rod 200 is in contact with an electrical power supply unit 206 extending from the upper portion of the vertical frame 204. As shown in FIGS. 6 and 7, the power supply unit 206 and the contact rod 200 serve to supply electrical current to a motor 39 for rotating rollers 41 which support the culturing containers and rotate the culturing containers about their axes in the culturing rack 5. The motor 39 and the rollers 41 will be described in detail later. Each of the culturing racks 5 has a lower surface provided with a roller 34 which runs on a rail 32 installed on a floor.

As shown in FIGS. 4 through 6, elongated chain C is fixedly secured to a lower inside face of each of the racks 5. Each of the chains C is connected together by a pin a. Each of the pins a is engageable with a recess 36a formed at a corner portion of the hexagonal sprocket 36. The elongated chain and the recess 36a of the sprocket 36 define a temporarily stational position of the rack 5 as shown in FIG. 5 when one of the racks 5 is at a position completely confronting the one side of the sprocket 36. The sprocket 36 is connected to a drive motor M through an endless chain 203. Upon rotation of the motor M, each of the culturing racks 5 is displaceable on a loop tracking rail 32.

During travel of the culturing containers 1 from the handling station 2 to the infeed station 4, the containers 1 are maintained in upstanding posture on the infeed conveyor 3 which extends out of the handling station 2. Between the handling station 2 and the infeed station 4 and on the path of the conveyor 3, a star wheel 8 is disposed which has five recesses successively formed on the circumferential surface thereof so as to provide a predetermined distance by every five culturing containers and to simultaneously supply a group of the five culturing containers 1 into a single rack 5.

Each of the rack stages can receive therein five culturing containers 1 from the infeed station 4, and two culturing racks 5 confront the infeed station, so that ten culturing containers 1 can be simultaneously transferred into the culturing racks 5.

Infeed Station

Figure 8:
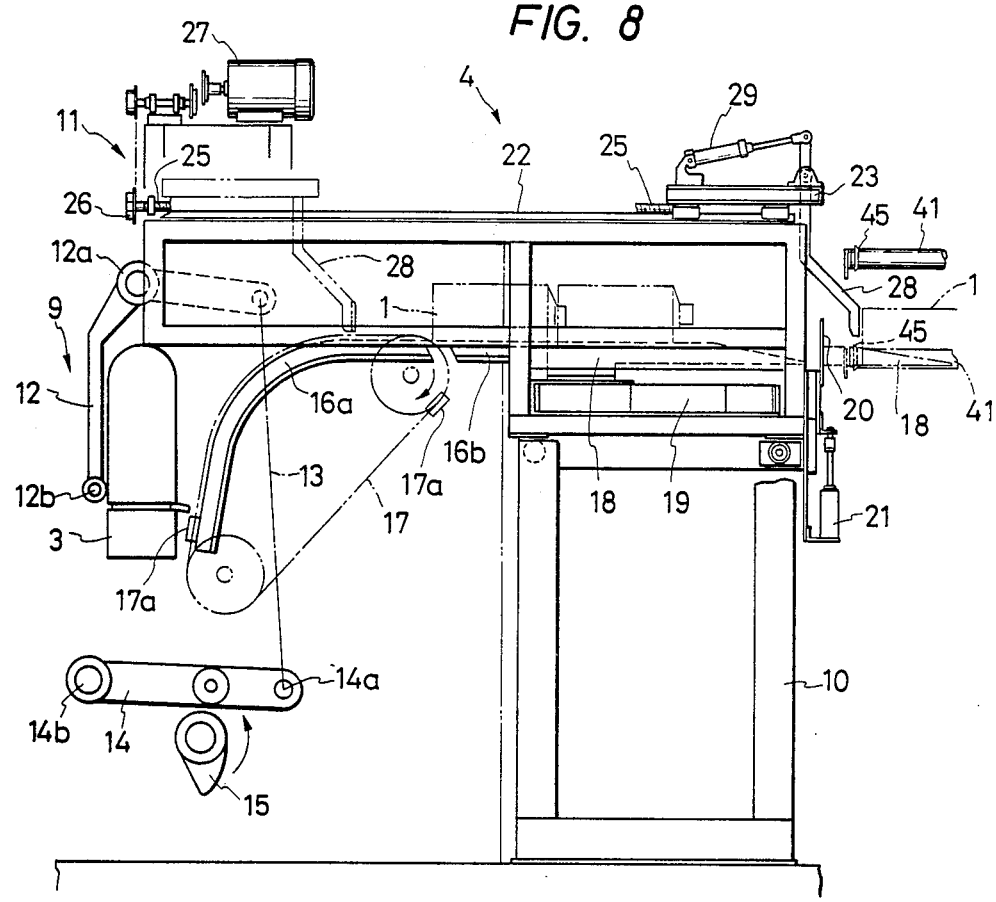

As shown in FIGS. 7 and 8, the infeed station 4 generally includes a posture changing mechanism 9, an infeed lifter 10 and a push-out mechanism 11. The posture changing mechanism is adapted to fall down the upstanding containers 1. The infeed lifter 10 mounts thereon the two containers oriented in a horizontal direction and axially aligned with each other, and moves the two containers into a vertical direction. The push-out mechanism 11 is disposed on the infeed lifter 10 and is adapted to push the culturing containers 1 toward the culturing racks 5. The push-out mechanism 11 is vertically movable in accordance with the vertical movement of the infeed lifter 10, while the collapsing mechanism 9 is not movable to a in vertical direction.

The posture changing mechanism 9 is disposed opposite the culturing racks 5 with respect to the infeed conveyor 3, and includes an infeed pusher 12, a swing arm 14, a cam member 15, guide members 16a and a chain 17. The infeed pusher 12 has a longitudinal center portion 12a rotatably supported so as to simultaneously fall down ten upstanding culturing containers 1 toward the culturing racks 5. The swing arm 14 has one end 14a connected to the end of the infeed pusher 12 through a linking rod 13, and another end 14b rotatably supported. The intermediate portion of the swing arm 14 is in contact with the cam member 15 so as to provide pivotal movement of the swing arm 14, to thereby swing the infeed pusher 12 about the pivot portion 12a. Each of the guide members 16a has a quadrant shape and has triangular cross-section. Neighbouring two guide members define a triangular valley portion on which the culturing container is supported. The chain 17 is driven along the arcuate path of the guide member 16a, and has a dog (support plate) 17a extending outwardly from the chain 17.

Figure 9:
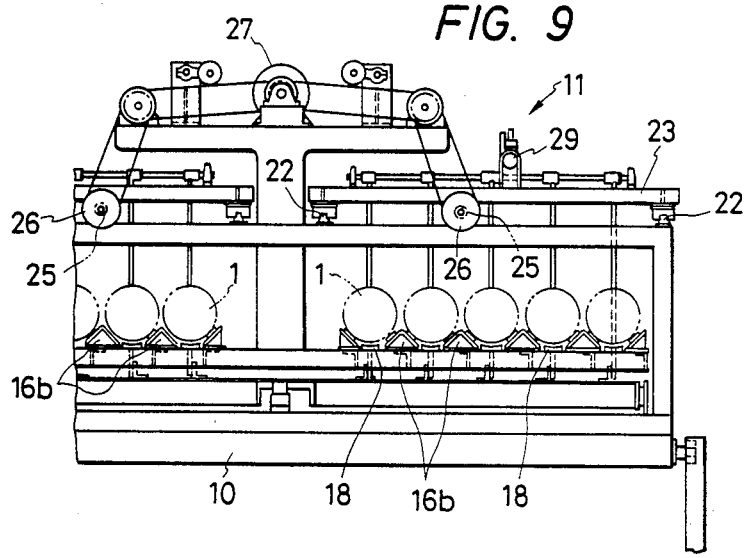
FIG. 9 is a front elevational view showing an infeed lifter.

With the structure, upon rotation of the cam member 15, the swing arm 14 in contact therewith is vertically pivoted about the end 14b, so that the lower end 12b of the infeed pusher 12 is pivoted, through the connecting rod 13, about the central portion 12a, and is displaced toward the culturing container 1 mounted in an upstand position on the infeed conveyor 3. As a result, the side wall of the culturing containers 1 are pushed by the lower end 12b, and the containers are fallen down toward the guide members 16a. Each of the ten containers is fallen down and is supported by neighboring two guide members 16a as shown in FIG. 9. By the movement of the chain 17, the dog 17a supports the bottom portion of each of the containers 1, and the containers change their angular orientation by 90 degrees from upstanding state to lying state during their travel along the guide members 16a. The lying containers are then supplied to an upper surface of the infeed lifter 10.

Figure 12:
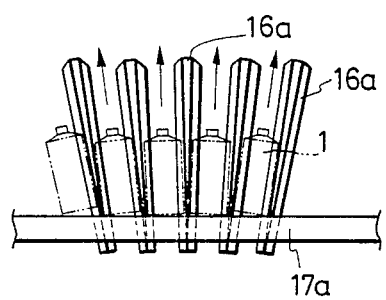
FIG. 12 shows an arrangement of guide members.

As shown in FIG. 12, the guide members 16a do not extend in parallelism from one another, but extend obliquely so that spaces defined between the neighboring guide members 16a are gradually increased toward the infeed lifter 10. Since a plurality of guide members 16b (FIG. 8) provided on the infeed lifter 10 are disposed separately at a pitch, two neighboring containers 1 are held separately from each other (FIG. 9).

Two axially aligned culturing containers 1 in their lying states are mounted on the infeed lifter 10 by the twice operations of the position changing mechanism 9. The infeed lifter 10 is vertically movable, so that the containers 1 mounted thereon are brought into a position coincident with the vertical position of the desired stage of the rack 5. At upwardly displaced position of the lifter 10, containers 1 are transferred into rack 5.

In the infeed lifter 10, disposed are guide members 16b for supporting the containers 1 with a space therebetween in lateral direction. The guide members 16b are disposed in alignment with the guide members 16a, and, a transferring plate 18 is disposed at a space defined between the neighboring guide members 16b. Each of the transferring plates 18 is provided with a recessed portion 18a having arcuate cross-section for avoiding displacement of the containers in radial direction thereof when the culturing container 1 is displaced from the infeed lifter 10 to the culturing rack 5 by means of the push-out mechanism 11. The transferring plate 18 has a tip end portion 18b provided with acute edge. The transferring plate 18 is movable toward the culturing racks 5 in a longitudinal direction of the plate 18 by a drive cylinder 19.

Figure 15:
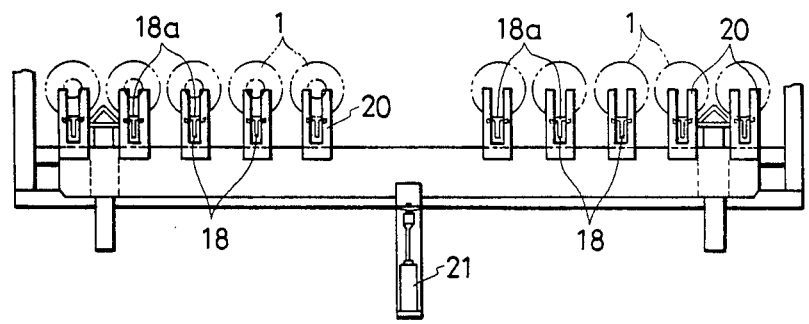
FIG. 15 is a front elevational view showing an infeed stop member.

The infeed lifter 10 also includes a infeed stop member 20 at a position in confrontation with the transferring plate 18 so as to restrain frontward displacement of the culturing containers 1. Further, a power cylinder 21 (FIG. 15) is provided to vertically move the infeed stop member 20 so as to selectively provide free movement of the container 1.

Figure 10:
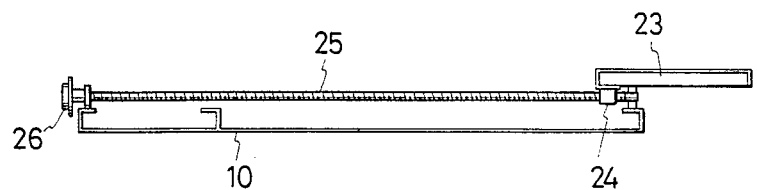
FIG. 10 is a side view showing a push-drive mechanism mounted on the infeed lifter.
Figure 11:
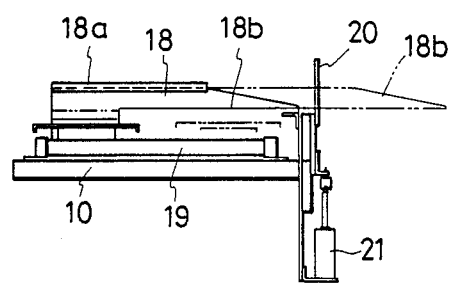
FIG. 11 is a side view showing transferring plates disposed on the infeed lifter.

The push-out mechanism 11 is shown in FIGS. 8 through 10. The push-out mechanism 11 includes an infeed slider 23, a nut 24, a ball screw 25, a pulley 26, a motor 27, an infeed member 28, and a power cylinder 29. The infeed slider 23 is slidably movable toward the culturing racks 5 on a guide rail 22 installed on the upper surface of the infeed lifter 10. The nut 24 is integrally provided to the infeed slider 23, and is threadingly engaged with the ball screw 25. The ball screw 25 has one end portion provided with the pulley 26 which is rotatable by the motor 27 through an endless belt. The infeed member 28 is positioned integrally with and in front of the infeed slider 23 and is adapted to push the bottom of the rear culturing container 1 of the axially aligned two containers. The cylinder 29 is adapted to move the infeed member 28 in vertical direction. Here, the terms "front" and "rear" imply the closer and furthest positions, respectively, with regard to the racks 5.

In the push-out mechanism 11, upon rotation of the motor 27, the infeed slider 23 is slid toward the culturing racks 5, so that the axially aligned two containers mounted on the infeed lifter 10 are urged toward the racks 5 by the infeed member 28.

Infeed operation of culturing containers 1 is carried out as follows:

First, the infeed conveyor 3 and the star wheel 8 are operated in order to supply two groups of containers 1, each group having five containers, to a given position in front of the infeed pusher 12 of the posture changing mechanism 9 and on the infeed conveyor 3. After acknowledgement of these containers at the given position, the movement of the infeed conveyor 3 is suspended.

Figure 13:
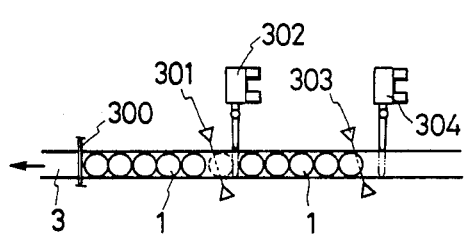
FIG. 13 is a top view showing arrangement of culturing containers upstandingly aligned one after another at the infeed station.

The two container groups can also be prepared by an alternative operation shown in FIG. 13. That is, movement of the leading container 1 is stopped by a stopping plate 300, and five containers of the first group are detected by a sensor 301. Upon this detection, a first stop unit 303 positioned adjacent the sensor 301 is operated to prevent the sixth container from its moving. Then, the succeeding four containers of the second group are detected by a sensor 303. When another five containers of the second group are detected, a second stop unit 304 is operated to prevent succeeding eleventh containers from moving. Therefore, two groups of the containers (totally ten containers) are aligned in front of the posture changing mechanism 9.

Then, the cam member 15 is rotated to allow the infeed pusher 12 to swing toward the guide members 16a, so that in total ten containers 1 fall down onto the guide members 16a.

Figure 14:
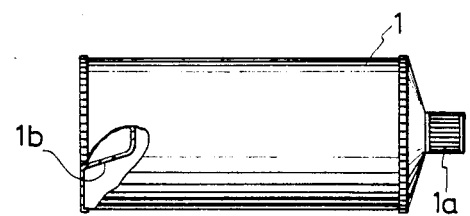
FIG. 14 is a side view of the culturing container partially cut away.

Thereafter, the chain 17 is driven to a first direction to simultaneously slide the ten containers 1 along the guide members 16a, so that upstanding containers 1 horizontally lay on guide members 16b of the infeed lifter 10. During travel of the containers, each of the container bottoms is held by the dog 17a of the chain 17 and are moved toward the rear portion of the infeed lifter 10 along the guide members 16a. Next, ten subsequent containers are introduced onto the guide members 16a and transferred onto the guide members 16b, during which each of the rear bottom ends of the already introduced ten containers are depressed by each of the front ends of the subsequent containers. As a result, two containers are axially aligned on the upper surface of the infeed lifter 10. In this instance, a cap 1a of the rear container 1 is inserted into a recessed portion 1b of a front container 1, so that the two containers are integrally aligned on the guide member 16b as shown in FIGS. 8 and 14.

The above operations are not interfered with by feed member 28, since member 28 is provisionally displaced at its ascent position. When two axially aligned containers are brought into the laying position, the infeed member 28 is moved to its descent position by the extension of the cylinder 29, and upon acknowledgement of the descent position, the infeed slider 23 is moved frontwardly toward the culturing racks 5. By the movement of the infeed slider 23, the infeed member 28 also moves to the same direction, so that the bottom portion of the rear container 1 of the axially aligned two containers are pushed by the infeed member 28. As a result, the two containers are moved toward the culturing racks 5.

In this instance, the infeed stop member 20 positioned in front of the containers is provisionally displaced at its ascent position. Therefore, the front end of front container 1 is brought into abutment with stop member 20 for positional adjustment. Concurrently, the movement of the infeed slider 23 is terminated.

Each of containers 1 is supported by guide members 16b, while the front end of the front container 1 is in abutment with infeed stop member 20, and rear end of the rear container 1 is in abutment with feed member 28. Therefore, each of the containers 1 is held in a stationary state in the infeed lifter 10 without an axial and lateral displacement. Such non-shiftable containers are then moved to their ascent position by the upward movement of the infeed lifter 10 by a vertical height coincident with that of the desired one of the stages of the rack 5 into which the containers are to be inserted.

The upward movement of the infeed lifter 10 is stopped, and the stop member 20 is moved to its descent position to release the fixing of the containers. At the same time, the transfer plate 18 is moved frontwardly (toward the rack 5) by the actuation of the cylinder 19. In this case, the motor 39 for rotating rollers 41 mentioned later in the culturing rack 5 is deenergized.

Figure 16:
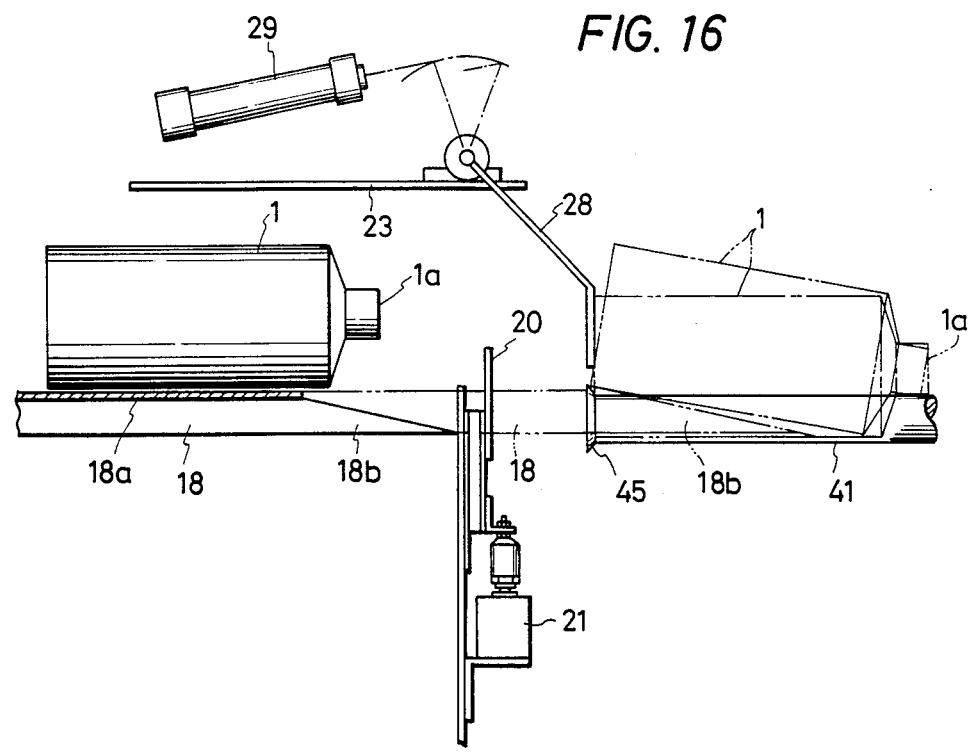
FIG. 16 is an explanatory illustration showing a transfer of the culturing container from the infeed lifter to the rack.
Figure 17:
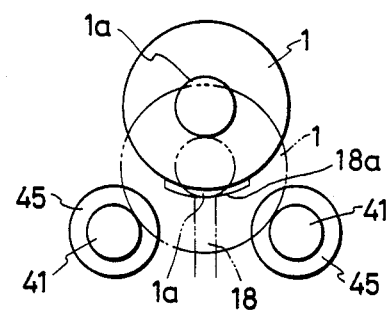
FIG. 17 is an explanatory illustration as viewed from a front side of the container in its transferring state shown in FIG. 16.
Figure 20:
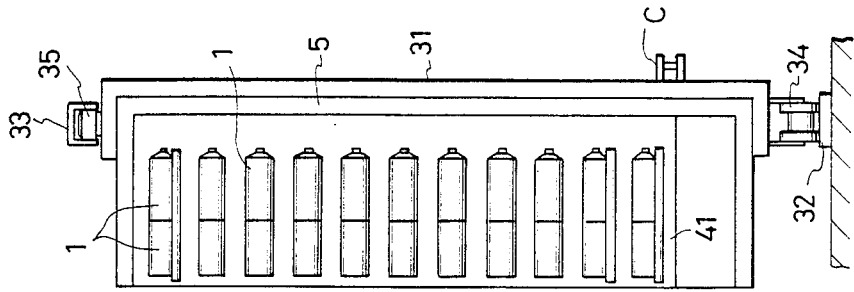
Figure 19:
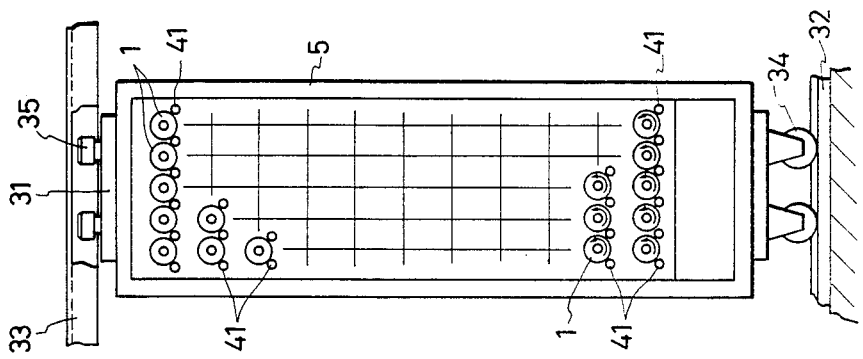
FIG. 19 is a front elevational view showing the culturing rack; and, FIG. 20 is a side elevational view of the rack shown in FIG. 19.

Referring in detail with the transferring plates 18, as shown in FIGS. 16 and 17, longitudinal axis of each of the transferring plates 18 extends along an intermediate space defined between the adjacent two rollers 41 and 41. Even though each of the rollers 41 is provided with two flanges 45, 45 at two front and rear sides thereof, the rear flange 45 does not prevent the transferring plate 18 from extending into the space and from moving between the rollers 41 and 41, because of the above-mentioned positional relationship between the rollers 41 and the plate 18.

After the transferring plate 18 exceeds the flange portion 45 and extends to a predetermined axial position of the space between the rollers 41 and 41, the forward movement of the transferring plate 18 is terminated. After acknowledgements of the advanced position of the transferring plate 18 and the descent position of the infeed stop member 20, the infeed feeder 22 is moved frontwardly (toward the culturing rack 5) to slide the culturing containers with respect to the guide plates 16b, so that the containers 1 are brought into the positions of the rollers 41. During the container travel from the guide plate 16b to the roller 41, the containers are supported by a recessed portion 18a of the transferring plate 18. Therefore, the containers can be smoothly transferred without their lateral displacement. Further, the transferring plate 18 prevents the front end of the container from abutting against the flange 45 of the roller 41.

When the front end of the front container 1 is brought into abutment with a rack stop member 46 (FIG. 22), and front end of the infeed member 28 slightly exceeds the flange 45 of the roller 41, the position of the feed member 28 is acknowledged, and the movement of the infeed slider 23 is stopped, and thereafter, the transferring plate 18 is retracted to a direction opposite the rack.

During the retracted movement of the transferring plate 18, the rear end of the rear container 1 is in abutment with the infeed member 28. Therefore, the infeed member 28 prevents the container 1 from axially moving rearward direction due to the retracting movement of the transferring plate 18. Instead, the containers are dropped onto the rollers 41 and 41, and are supported thereby. Further, since the front end of the infeed member 28 is positioned frontward manner with respect to the flange 45, the rear end of the rear container 1 is also downwardly positioned in front of the flange 45. As a result, the containers 1 are supported by the flange 45 and the stop member 46 without any axial displacement. Such successive operations are performed without any trouble.

Then, the infeed slider 23 is moved rearward direction (toward the posture changing mechanism), and the infeed lifter 10 is moved to its original descent position for receiving new ten containers 1 therein. Upon receipt of the containers, the infeed lifter 10 is again moved upwardly to a predetermined new stage of the rack 5 for inserting the containers to the selected stage of the rack 5. Such infeed operations are repeatedly carried out, and, accordingly, completed with the insertion of the culturing containers into the culturing racks 5 by means of the infeed station 4.

Figure 18:
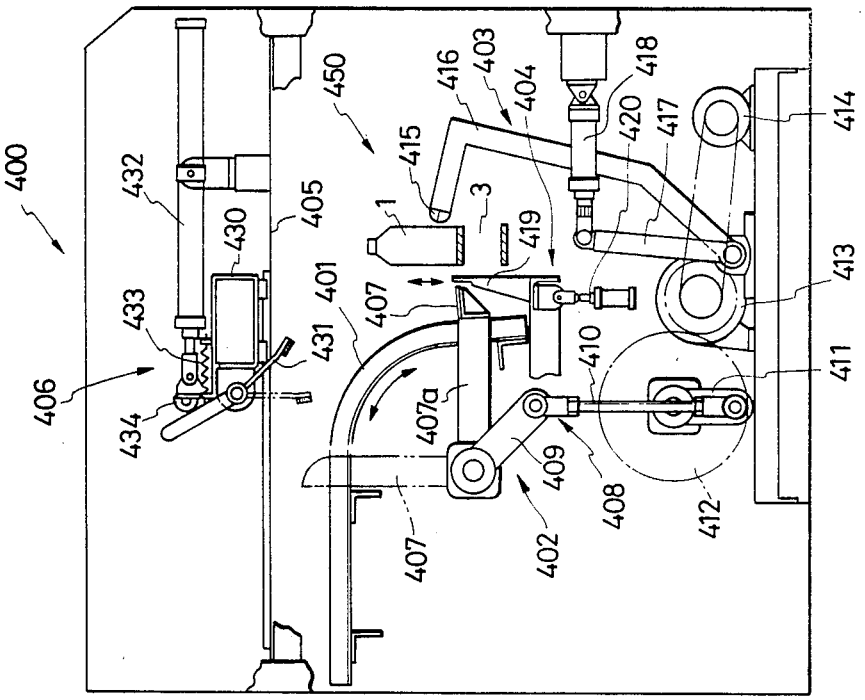
FIG. 18 is a side view showing an infeed station according to a modified embodiment of this invention.

An infeed station 400, according to another embodiment of the present invention, will be described with reference to FIG. 18. The infeed station 400 generally includes a posture changing mechanism 450 (corresponding to the posture changing mechanism 9 of the first embodiment), and a push-out mechanism 406 (corresponding to the push-out mechanism 11 of the first embodiment). The posture changing mechanism 450 comprises an infeed pusher 403, the guide member 401, a container supporting unit 404 and a container infeeding unit 402 (corresponding to the push-out mechanism 11 of the first embodiment). The infeed pusher 403 is adapted to push and fall down the containers on the infeed conveyor 3 toward the guide members 401. The container infeeding unit 402 is adapted to supply containers 1 along guide members 401 into the infeed lifter 10 by a reciprocally swing rotation. The container supporting unit 404 is protrudable to the upper space of the conveyor 3 to support side walls of the containers 1 for preventing the containers from their falling down on the conveyor 3 during their state shown in FIG. 13, when ten containers are arranged in line with their upstanding positions on the conveyor 3. The push-out mechanism 406 is provided on the infeed lifter 10, and is slidable on a slide surface 405. The push-out mechanism 406 pushes the containers lying on a horizontal portion of the guide member 401 and on the infeed lifter 10 toward predetermined stage of the culturing rack 5 disposed at the left margin of FIG. 18.

The container infeeding unit 402 includes a supporting plate 407, support arms 407a, and a crank mechanism 408. The supporting plate 407 extends in a direction across the guide members 401 for supporting bottom portions of the containers at a position outside the guide members 401. The support arms 407a are provided at the opposite ends of the supporting plate 407. The support arms 407a are operably connected to the crank mechanism 408, so that the support arms 407a are reciprocally rotatable within an angular 90 degrees between the horizontal position and the vertical position as shown by solid line and two-dotted chain line. The crank mechanism 408 includes first, second and third links 409, 410 and 411. The third link 411 is rotated together with the rotation of a first gear wheel 412 which is in meshing engagement with a second gear wheel 413 drive rotated by a motor 414 through a power transmission belt.

The infeed pusher 403 includes a push rod member 415, first swing arms 416, a second swing arm 417, and a cylinder 418. The push rod member 415 extends in a transverse direction of the overall device and has a length larger than the outer diameters of the ten containers, so that upstanding containers can be pushed simultaneously by the push rod member 415. Each of the first swing arms 416 has an upper end connected to the each end of the push rod member 415, and a lower end connected to a lower end of the second swing arm 417. The upper end of the second swing arm 417 is connected to the cylinder 418. Upon extension and retraction of a rod of the cylinder 418, the first swing arm 416s are moved toward and away from the containers upstanding on the infeed conveyor 3.

The container supporting unit 404 is disposed between the infeed pusher 403 and the container infeeding unit 402. The container supporting unit 404 includes a container supporting plate 419 projecting in vertical direction and extending in transverse direction of the overall device, and a cylinder 420 for moving the supporting plate 419 in vertical direction. The container supporting plate 419 is maintained at its ascent position, so that it extends in parallel with the rows of the guide members 401 until the upstanding ten containers on the infeed conveyor 3 are aligned in line without offset of one or several one of the containers. That is, as shown in FIG. 13, the containers 1 are subjected to force which restrains their travel on the infeed conveyor 3 by the stop plate 300. Therefore, the containers 1 on the conveyor 3 are urged to be in close contact with each other. In this state, if one of the containers is moved to the offset position, containers may be fallen down, and dropped from the conveyor 3. To avoid this, the container supporting plate 419 is disposed. The container supporting plate 419 is retracted to its descent position when the infeed pusher 403 urges the containers toward the guide members 401, so that the pushing operation by the push rod member 415 is not disturbed by the container supporting plate 419.

The push-out mechanism 406 includes a slide frame 430 slidably movable on a slide surface 405, an infeed member 431 swing provided on the slide frame 430 for abutting the bottom surface of the container 1 and pushing the same, and a power cylinder 432 for moving the slide frame 430. The infeed member 431 is urged toward a direction for providing its vertical position (operable position) shown in a chain line by biasing force of a spring 433. When the infeed member 431 is in a position shown by the solid line, the infeed member 431 abuts a stop member 434 protruding from the frame member of the infeed lifter 10, so that the infeed member 431 is maintained at its inoperable position where the infeed member 431 does not prevent the containers running along the guide members 401 from their moving toward the culturing rack 5. That is, if the cylinder rod of the cylinder 432 is extended, the infeed member 431 is moved away from the stop member 434. Therefore, the infeed member 431 is rotated to a vertical operable position shown by the chain line by the biasing force of the spring 433. As a result, containers on the horizontal portion of the guide members 401 and on the infeed lifter 10 are pushed toward the rack 5 by the vertically oriented infeed member 431.

Culturing Rack

The culturing racks 5 are assembled at internal space of rack frame 31 of the rack supporting apparatus S as shown in FIGS. 19 thru 25.

In the interior of the culturing rack 5, provided is a rotation mechanism 37 for rotating the culturing container 1 about its axis and for promoting culturing of the cells contained therein.

The rotation mechanism 37 includes a motor 39, a deceleration unit 38 connected to the motor 39, a rotary shafts 40 rotatable by the rotation of the motor 39, and rollers 41 rotatable by the rotary shafts 40, the rollers 41 mounting thereon culturing containers 1 for rotating the latter about their axes.

Six rotary shafts 40 are arranged in line and in parallelism in horizontal direction as best shown in FIG. 16, whose number is equal to the number of the rollers 41. One of the rotary shafts 40 is integrally provided with a pulley 42 which is rotatable by the rotation of the motor 39 through a belt 43a. By the rotation of the one of the shafts 40, other rotary shafts 40 are rotated through a power transmission belt 43b. Further, a belt 44a is mounted between each of the rotary shafts 40 and each of the upper adjacent rollers 41. Furthermore, a belt 44b is mounted between each of the rollers 41 and each of the upper neighboring rollers 41 as shown in FIG. 22. Therefore, the rotation of the rotary shaft 40 is transmitted successively to the upper adjacent rollers 41 through the belts 44a and 44b.

In the rack 5, six rollers 41 are arranged in line and in parallelism in horizontal direction, and ten stages of roller arrangements are provided in vertical direction. Therefore, totally 60 rollers 41 are rotatably disposed in the rack 5. Each one of the culturing containers 1 is supported by neighboring two rollers 41, and therefore, five containers 1 are supported in the single stage. Thus supported containers are rotatable about their axes by the rotation of the rollers 41.

Figure 25:
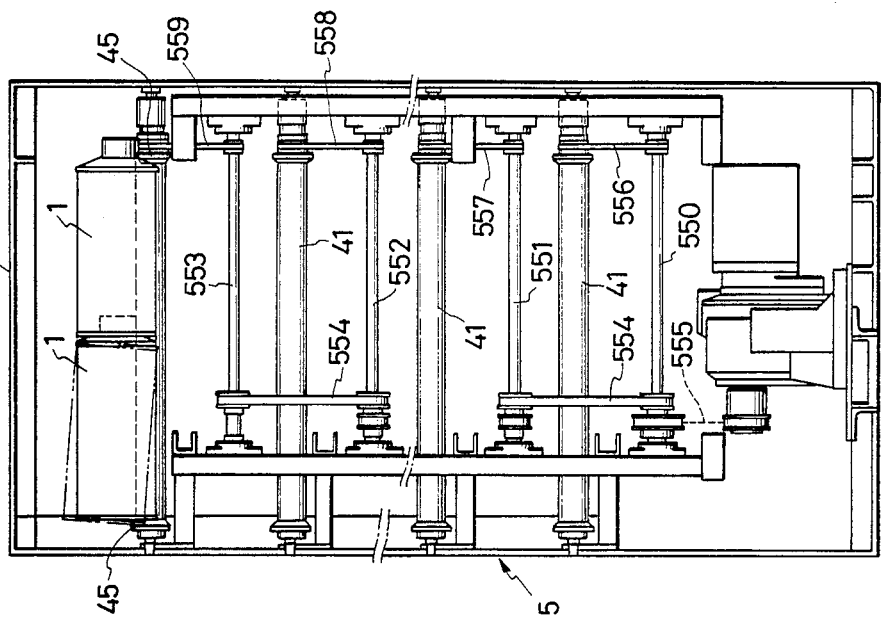
FIG. 25 is a side elevational view showing the roller driving mechanism shown in FIG. 24.
Figure 24:
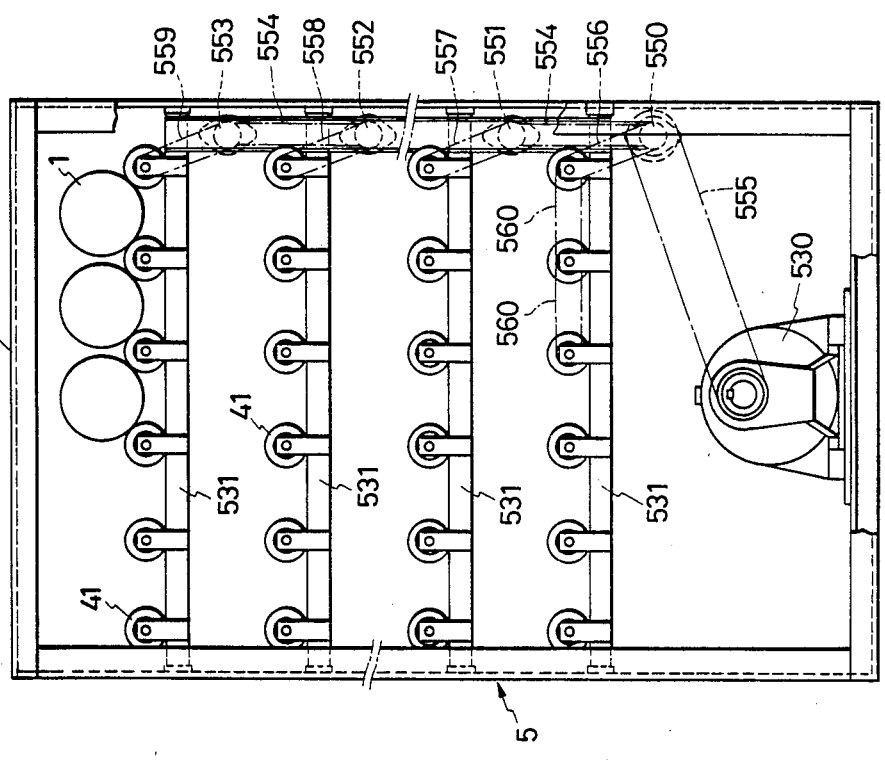
FIG. 24 is a front elevational view showing a mechanism for driving rollers in the rack according to a modified embodiment of this invention.

Modification to the culturing rack 5 is shown in FIGS. 24 and 25. In the modified embodiment, the culturing rack 5 has a frame member F in which a plurality of supporting racks 531 are secured. On each of the supporting racks 531, there are provided a plurality of rollers 41. Each of the culturing container 1 (roller bottle) is supported by the neighboring two rollers 41. A culturing motor 530 is installed at the lower portion of the rack 5. The rotation of the culturing motor 530 is transmitted to the rollers 41 of each stage through power transmission means. The power transmission means includes elongated shafts 550, 551, 552, 553 extending along a side wall of the frame F. Belts 554 and 554 are disposed between the shafts 550 and 551 and between the shafts 552 and 553, respectively. The elongated shafts 550, 551, 552 and 553 are provided in accordance with the support racks 531. The rightmost rollers 41 in the support racks 531 are connected to the elongated shafts 550, 551, 552 and 553 through belts 556, 557, 558 and 559, respectively. The motor 530 is connected to the lowermost elongated shaft 550 through a power transmission belt 555. The rollers on the identical supporting rack 531 are connected together to the rightmost roller 41 by belts 560 and 560. Therefore, all rollers 41 are rotated about their axes in the same direction. Both axial end portions of the roller 41 are provided with flanges 45 and 45 between which two culturing containers (roller bottles) connected together and axially aligned with each other are rotationally supported.

Discharge Station

Figure 26:
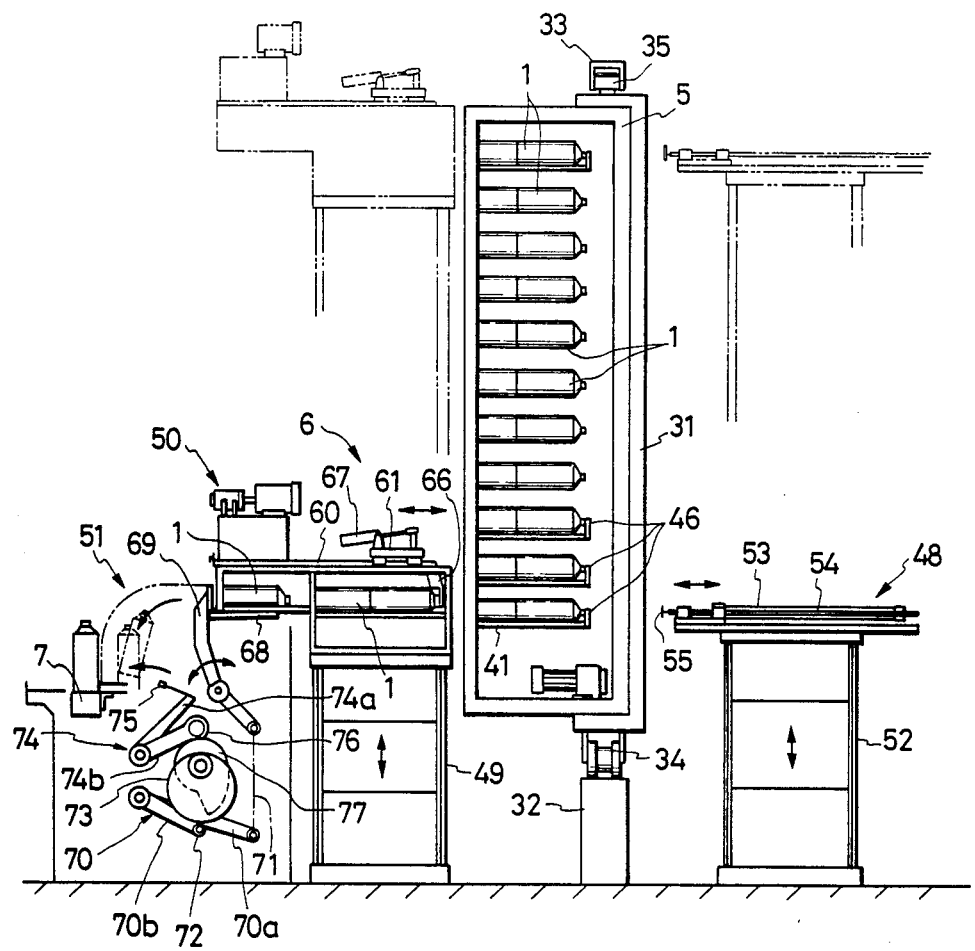
FIG. 26 is a side elevational view showing the discharge station.
Figure 27:
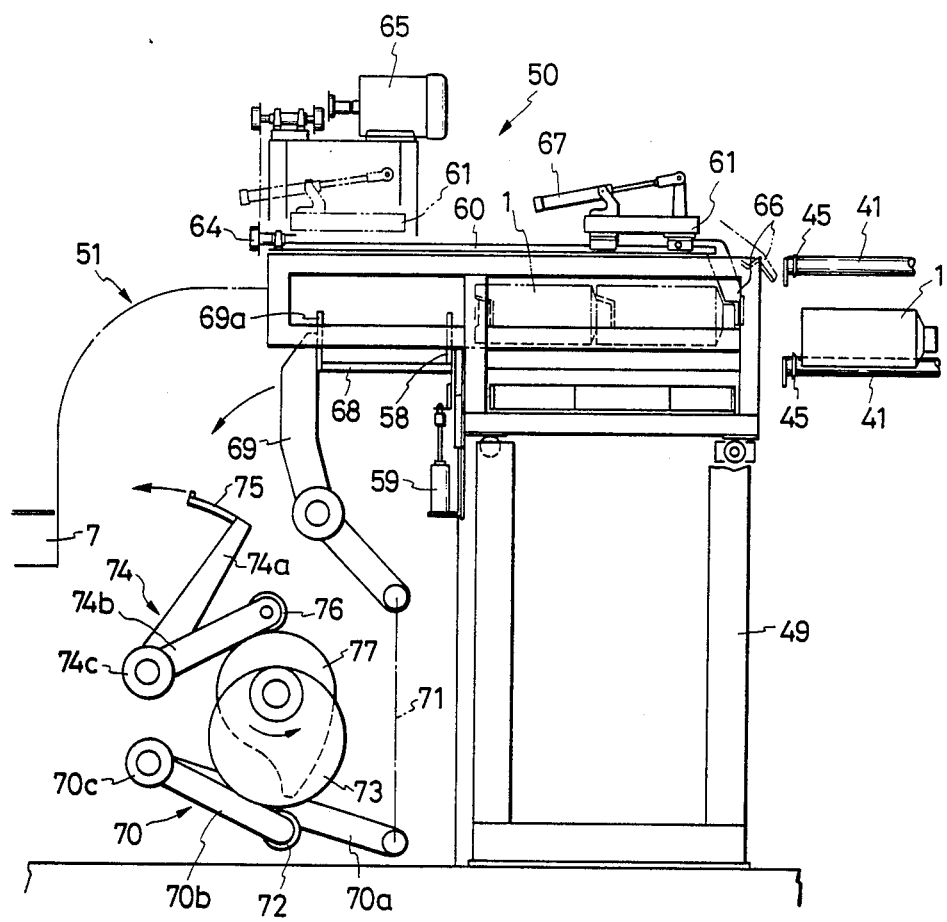
FIG. 27 is an enlarged side elevational view showing a discharge lifter in the discharge station.

The discharge station 6 shown in FIGS. 26 thru 27 generally includes a discharge mechanism 48, a discharge lifter 49, a clearing mechanism 50 and an upstanding mechanism 51. The discharge mechanism 48 is adapted to take out the culturing containers from the culturing rack 5. The discharge lifter 49 is adapted to mount thereon the culturing containers discharged from the rack 5 by the discharge mechanism 48, and to displace them in vertical direction. The clearing mechanism 50 is disposed on the discharge lifter 49 for clearing the culturing containers mounted on the discharge lifter 49. The upstanding mechanism 51 is adapted to receive containers discharged out of the discharge lifter 49 and to permit the containers to be at their upstanding positions.

The discharge mechanism 48 includes an elevation member 52 vertically movable, a power cylinder 53 mounted on the elevation member 52 and a push rod 55 extending in the axial direction of the lying containers into the rack 5 and movable in axial direction thereof along a guide rod 54. The discharge mechanism 48 is disposed at a position opposite the discharge lifter 49 with respect to the rack 5.

After the elevation member 52 is elevated to a predetermined position at which there is one of the stages of the rack storing the containers to be discharged, the cylinder 53 is actuated to move the push rod 55 in a frontward direction (toward the culturing rack 5), so that a plate the push rod 55 abuts the front end of the front containers in the rack 5. When the push rod 55 is further moved, the containers are moved toward the discharge lifter 49, and are placed on the upper surface thereof.

Figure 28:
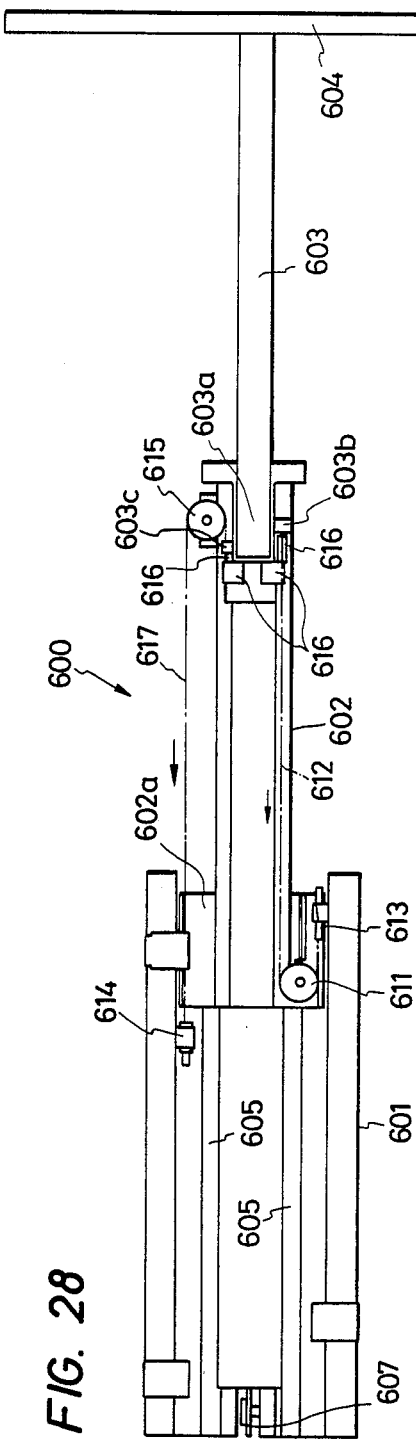
FIG. 28 is a plan view showing a telescopic discharge mechanism; and, FIG. 29 is a side view of the telescopic discharge mechanism shown in FIG. 28.
Figure 29:
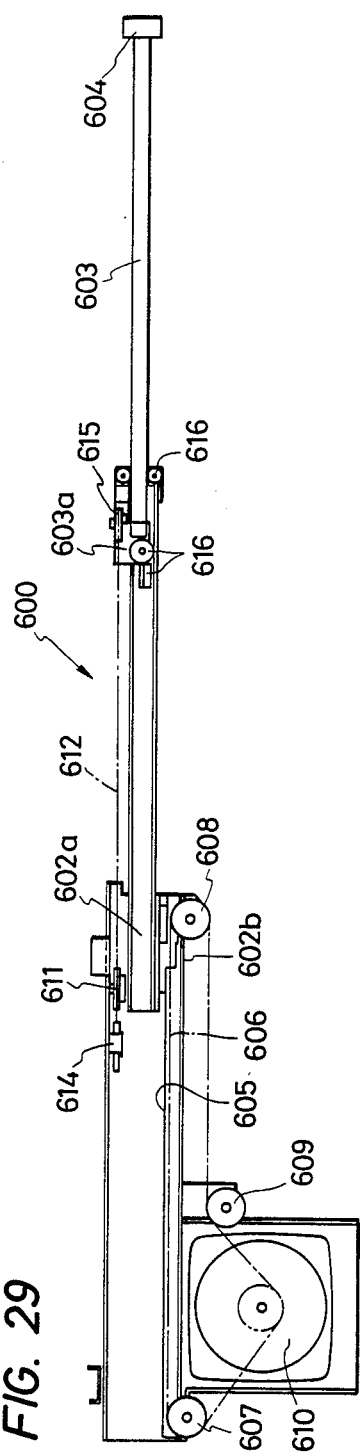

Instead of the above-described discharge mechanism 48, a telescopic discharge mechanism 600 shown in FIGS. 28 and 29 is used. The telescopic mechanism 600 has double stage telescopic movement to minimize axial length upon retraction thereof, so that the mechanism 600 can be installed within a rack supporting apparatus S having small transversal width. Therefore, resultant apparatus can provide a compact overall size.

In FIGS. 28 and 29, the telescopic discharge mechanism 600 includes a main frame 601 in which a slide flame 602 is disposed in a sliding manner extendable and retractable with respect thereto. Further, within the slide flame 602, a push rod 603 is disposed in a sliding manner extendable and retractable with respect thereto. A free end of the push rod 603 is fixed with a pushing plate 604 by which culturing containers 1 are pushed toward the discharge lifter 49. The main frame 601 is provided with rails 605 605 at a bottom surface thereof, and a lower surface of the slide frame 602 is in slide contact with the rails. Pulleys 607 and 608 are provided at both longitudinal ends of the main frame 601, and a drive motor 610 is disposed below the main frame 601. A chain 606 is mounted between the pulleys 607 and 608 and is driven by the motor 610. One longitudinal base end (left side end in FIG. 28, or rear end) 602a of the slide frame 602 is integrally provided with a protrusion 602b which is coupled to the chain 606. Incidentally, the drive chain 606 is subjected to tension control by a tension pulley 609.

A pulley 611 is provided at the base end 602a of the slide frame 602, and the pulley 611 is engaged with a chain 612. One end of the chain 612 is fixedly secured to the front end of the main frame 601 by means of a fixing member 613 extending from one side surface of the frame 601, while another end of the chain 612 is fixedly secured to a fixing member 603b fixed to a rear base end 603a of the push rod 603. With the structure, the chain 612 is normally urged toward the rear end of the main frame 601, i.e., leftwardly in FIG. 28. Further, a pulley 615 is provided at the front end of the slide frame 602, and the pulley 615 is engaged with a chain 617. One end of the chain 617 is secured to a fixing member 614 extending from another side surface of the main frame 601, while another end of the chain 617 is secured to a fixing member 603c fixed to the rear base end 603a of the push rod 603. With the structure, the chain 617 is normally urged toward the rear end of the main frame 601, i.e., leftwardly in FIG. 28. A pair of guide rollers 616, 616 are rotatably supported to the rear base end 603a of the push rod 603. The guide rollers 616 are in rolling contact with an internal surface of the slide frame 602, so that the push rod 603 is smoothly movable relative to the slide frame 602.

The motor 610 is a reversible motor. If the reversible motor 610 is rotated in a counterclockwise direction in FIG. 29. The slide frame 602 is moved toward left because of the coupling engagement between the chain 606 and the protrusion 602b. By the leftward movement of the slide frame 602, the pulley 616 at the rear base end 603a is urged leftward, so that the pulley 615 is also moved leftward. Therefore, the push rod 603 is retracted into the slide frame 602 in response to the leftward movement of the slide frame 602. During this movement, a partial length of the chain 617 between the pulley 615 and the fixing member 603c is gradually increased in accordance with the retraction of the push rod 603 into the slide frame 602. Thus, when the rear base end 602a of the slide frame 602 is reached to the rear end of the main frame 601, both slide frame 602 and the push rod 603 are simultaneously accommodated within the main frame 601.

If the reversible motor 610 is rotated in clockwise direction in FIG. 29, the slide frame 602 is moved rightward in the Figure, so that the pulley 611 is moved rightward for relaxing the tension applied to the chain 612. Accordingly, the chain 617 drives the base rear end 603a of the push rod 603 rightward, so that the push rod extends out of the slide frame 602, whereby containers are pushed toward the discharge lifter.

Figure 30:
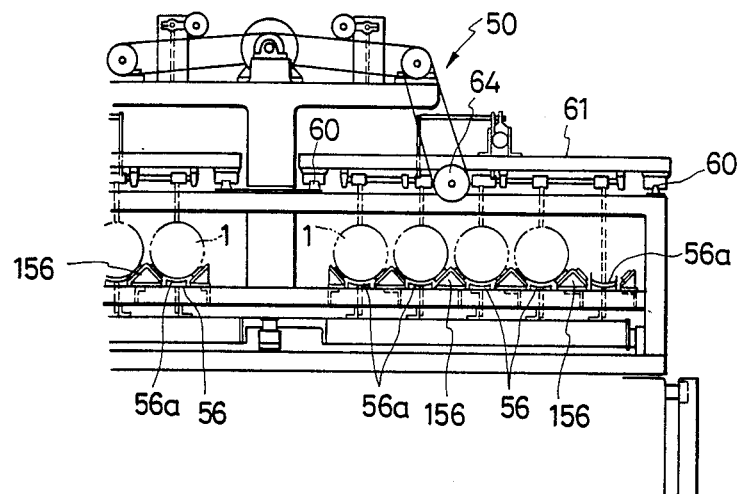
FIG. 30 is a front elevational view showing a discharge lifter.
Figure 31:
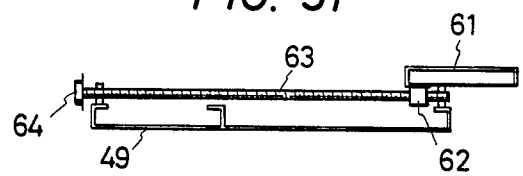
FIG. 31 is a side view showing a driving unit of a clearing mechanism mounted on the discharge lifter.

The discharge lifter 49 can be elevated at a position in alignment with the vertically elevated position of the elevation member 52. After the culturing containers 1 are moved from the culturing rack and mounted on the upper surface of the discharge lifter 49 by the operation of the discharge mechanism 48, the discharge lifter 49 is moved to its descent position. At the upper surface of the discharge lifter 49, there is provided transfer plates 56 movable toward and away from the rack 5 by a cylinder 57 for mounting the containers on recessed portion 56a (FIGS. 30 and 31) when the containers are transferred from the culturing rack 5 to the discharge lifter 48. The recessed portion 56a has arcuate cross-section for preventing the container from its lateral displacement, and has a front end portion 56b having arcuate edge shape similar to the transferring plate of the infeed lifter 10, which arcuate edge shape can allow the culturing container 1 to be smoothly discharged out of the culturing rack 5 without any mechanical interference with the flange 45 of the roller 41. Each of the transferring plates 56 is positioned at an intermediate position between the neighboring rollers 41 and 41 as shown in FIG. 23 similar to the transferring plates 18 of the infeed station 4. The transferring plates 56 extend into the inside of the culturing rack 5 without any interference with the flanges 45 of the rollers 41. Because of the advancing movement of the transferring plate 56, the rear end portion of the rear container 1 installed in the rack 5 is moved upward, since the container rear portion rides onto the inclination surface of the front end portion 56b of the transferring plate 56. The upward position is higher than the upper end position of the flange 45.

Figure 32:
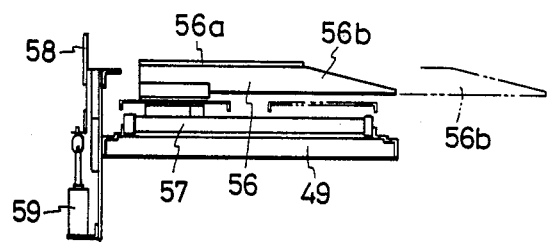
FIG. 32 is a side view showing transferring plates disposed on the discharge lifter.
Figure 33:
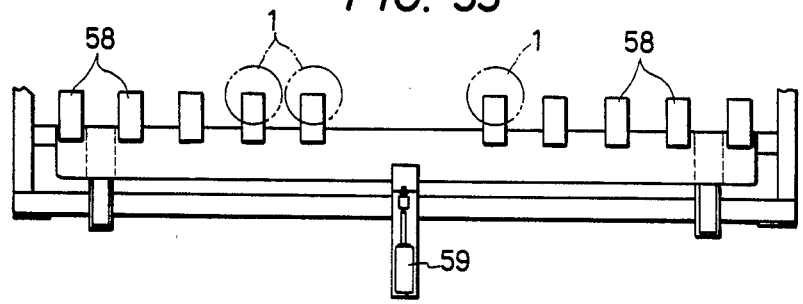
FIG. 33 is a front view showing a stop member fixed to the discharge lifter.

Inside the discharge lifter 49, there are provided a discharge stop member 58 at the rear side thereof to which the rear end of the rear container abuts for preventing the container from being dropped from the lifter 49, and a power cylinder 59 for vertically displacing the stop member 58 for selectively release the stop function of the stop member 58 (see FIGS. 32 and 33).

The clearing mechanism 50 has a construction substantially the same as that of the push-out mechanism 11 of the infeed station 4 as shown in FIGS. 27, 30, 31, 34 and 35, and includes a discharge slider 61, a nut 62, a ball screw 63, a pulley 64 a motor 65, a discharge feeder 66 and a cylinder 67. The discharge slider 61 is slidably disposed on a guide rail 60 fixed to an upper surface of the discharge lifter 49 and movable toward and away from the culturing rack 5. The nut 62 is integrally fixed to the discharge slider 61 and is threadingly engaged with the ball screw 63, so that the discharge slider 61 is movable by the rotation of the ball screw through the nut 62. The ball screw 63 has one end portion integrally provided with the pulley 64 which is driven by the rotation of the motor 65 through a belt. The discharge feeder 66 is positioned at front side of the discharge slider 61. The feeder 66 abuts the front end of the front culturing container 1 lying on the discharge lifter 49 and pushes the container toward the upstanding mechanism 51 for clearing the containers from the lifter 49. The cylinder 67 is provided for moving the feeder 66 in vertical direction.

In the clearing mechanism 50, the front end of the front container 1 is supported by the discharge feeder 66, and therefore, the containers lying on the discharge lifter 49 is prevented from being axially displaced even during descending motion of the lifter 49, and further, the containers are moved toward a plurality of receptacle bars 68 described later of the upstanding mechanism 51 by the rearward movement of the discharge feeder 66.

Figure 36:
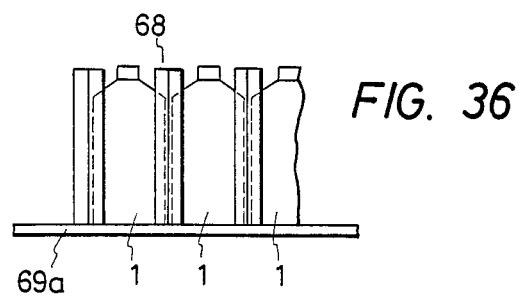
FIG. 36 is an illustration showing a front end part of the upstanding mechanism shown in FIG. 27.

The upstanding mechanism 51 includes a discharge arm 69, a cam link 70, a disc cam 73, a swing arm (clearing unit) 74 and a cam 77. The discharge arm 69 has, at its one end portion, a support plate 69a for abutting the bottoms of the containers 1 and for supporting the same, and the receptacle bars 68 each extending perpendicular to the support plate 69a and having triangular cross section for spaced for receiving of containers as shown in FIG. 36. When the upstanding mechanism 51 is coming to a position shown in FIGS. 26 and 27 for receiving containers from the discharge lifter 49, the receptacle bars 68 are positioned at the rear side of the discharge lifter 49. The discharge arm 69 has an intermediate portion rotatably supported, and another end portion (lower end portion) connected to the cam link 70 through a link member 71. The cam link 70 is provided with first and second rod members 70a and 70b. Rear ends of the rod members 70a, 70b are rotatably provided about an identical rotation axis 70c. A front end of the first rod member 70a is rotatably connected to another end portion of the discharge arm 69 through the link 71. A front end of the second rod member 70b is rotatably provided with a roller 72 with which the disc cam 73 is in camming contact. The swing arm 74 has first and second arm members 74a and 74b. One end of the arm members 74a and 74b are assembled together and rotatable about an identical axis 74c. A free end of the first arm member 74a is fixed with a push member 75 extending toward a discharge conveyor 7, and a free end of the second arm member 74b is rotatably provided with a roller 76. The cam 77 is in surface contact with the roller 76 and are rotatable together with the rotation of the disc cam 73.

With the structure, in the upstanding mechanism 51, when the discharge feeder 66 is moved rearward (away from the rack 5), the culturing container 1 is dropped onto the container receptacle bars 68 in its lying state as shown in FIG. 35. The discharge arm 69 is angularly rotated by 90 degrees in a counterclockwise direction in FIG. 27 because of the rotation of the disc cam 73. Therefore, the culturing container 1 maintained in the receptacle bars 68 is directed in its upstanding orientation. With maintaining this state, the push member 75 moves toward the discharge conveyor 7 by the rotation of the discharge cam 77, so that the side peripheral surface of each upstanding container 1 is urged toward the conveyor 7. The bottom end of the container is slidably moved and the container is rested on the conveyor 7 in its upstanding posture.

Container discharge operation is conducted according to the following procedures:

After the culturing rack 5 is moved to a predetermined position which confronts the discharge station 6, the position of the rack 5 is acknowledged, and the rotation of the drive sprocket 36 is suspended. Then the elevation member 52 and the discharge lifter 49 are elevated to a position corresponding to a desired stage of the rack 5, and the ascending movements of the member 52 and the lifter 49 are stopped.

Thereafter, the transferring plate 56 is moved in a frontward direction, and the discharge stop member 58 is moved to its ascent position, while rotation of the motor 39 for rotating the rollers 41 is suspended.

Then, the transferring plate 56 is moved in a frontward direction, so that the transferring plate 56 is inserted into a space defined between the neighboring rollers 41. As a result, the rear end portion of the rear container 1 is slidably elevated to a position higher than that of the upper end of the flange 45 along the front slanting portion of the front portion 56b of the transferring plate 56. The frontward movement of the transferring plate 56 is stopped at a predetermined position.

Incidentally, the front end of the front container may be urged frontward due to the frontward movement of the transferring plate 56. However, since the front end of the front container 1 is in abutment with the stop member 46 provided at the rack 5, frontward displacement of the container can be obviated.

The movement of the transferring plate 56 is stopped, and then the push rod 55 of the discharge mechanism 48 is moved toward the rack 5 and abuts the front end of the front container 1 lying in the rack 5. When the push rod 55 is further moved, the containers 1 slidably move with respect to the inclined surface of the front end portion 56b of the transferring plate 56. The push rod 55 continuously pushes the containers until the rear end of the rear container 1 abuts the stop member 58 positioned in a rearward direction with respect to the push rod 55. For enabling the above described operation, the discharge feeder 66 is maintained at its ascent position so as not to prevent the containers from moving.

Thereafter, the transfer plate 56 and push rod 55 are moved back to their original rest positions, and then, the discharge feeder 66 is moved to its descent position to support the front end of the front container 1 (FIG. 27). As a result, the container 1 is stationarily held by the discharge feeder 66, the stop member 58 and the transferring plate 56. Such stationary supporting manner is maintained during the descent movement of the elevation member 52 and the discharge lifter 49.

Then, the discharge stop member 58 is moved to its descent position for providing a support-free state to the containers 1. Simultaneously, the discharge slider 61 is moved toward the upstanding mechanism 51 after acknowledgement of the upper predetermined position of the supporting plate 68 for dropping the rear container thereon by its gravity as shown in FIG. 35. In this case, the front end of the rear container is loosely engaged with the rear end of the front container, and therefore, the rear container 1 is easily disengaged from the front container. The movement of the slider 61 is stopped at its intermediate position, and the discharge arm 69 is angularly rotated in a downward direction by 90 degrees, so that the container 1 is coming into its upstanding position on the support plate 69a. Thereafter, the push member 75 is extended through the receptacle bars 68 and pushes the side wall of the container 1 to discharge it onto the discharge conveyor 7 with maintaining upstanding position thereof.

The discharge arm 69 is rotated upwardly by 90 degrees to restore its stand-by position, and the discharge slider 61 is further moved from its intermediate position toward the upstanding mechanism 51, so that the front container is also dropped onto the receptacle bars 68 and is discharged to the conveyor 7. Prior to the discharge of the front container 1 toward the conveyor 7, the conveyor 7 is driven to displace the provisionally carried rear container 1 for providing a mounting space for the front container 1.

The above-described operations are repeatedly carried out with respect to each of the ten stages of the rack for discharging containers 1 installed on all ten stages of the rack 5 toward the discharge conveyor 7.

Figure 37:
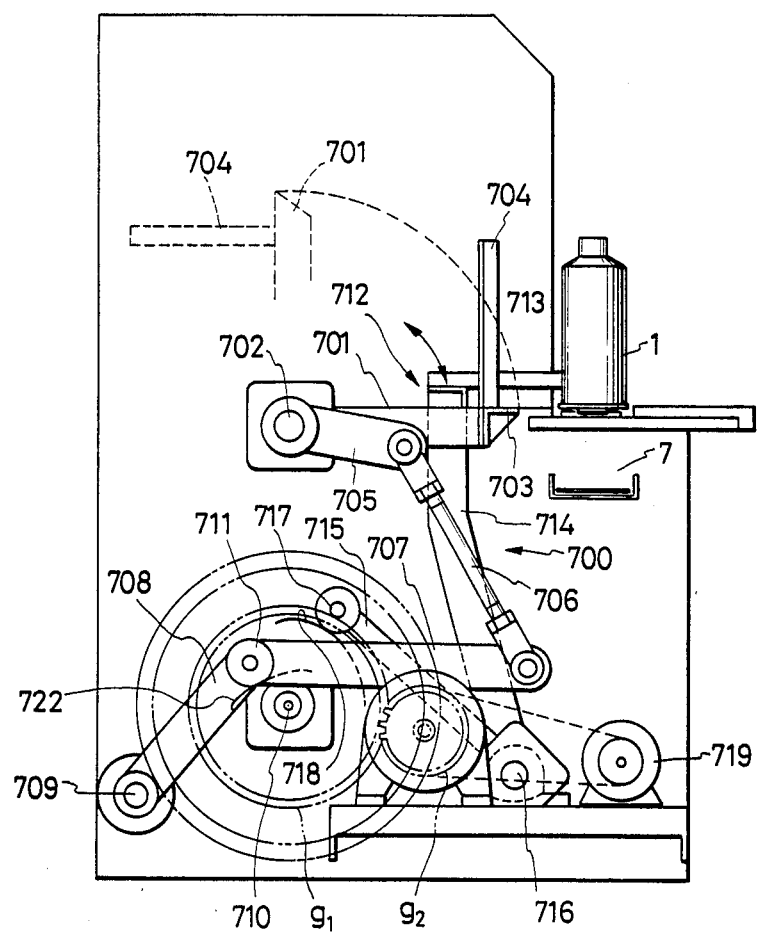
FIG. 37 is a side elevational view showing an upstanding mechanism according to a modified embodiment of this invention.

FIG. 37 shows an upstanding mechanism 700 according to another embodiment of this invention in the discharge station. The upstanding mechanism 700 includes a discharge arm 701 corresponding to the arm 69 shown in FIG. 26. The discharge arm 701 is swingable about a shaft 702, and a free end of the discharge arm 701 is provided with a supporting plate 703 and a receptacle bars 704. One end of a first link 705 is connected to the shaft 702, and another end thereof is rotatably connected to one end of a connecting rod 706. The connecting rod 706 has another end rotatably connected to one end of a second link 707 which end is rotatably connected to one end of a third link 708. Another end of the third link 708 is rotatably supported to a frame. The rotatable connecting portion between the second and third links 707 and 708 is provided with a cam follower 711 which is in surface contact with a cam surface of a cam member 722 rotatable about an axis of a shaft 710.

On the other hand, the containers 1 held by the receptacle bars 704 and the supporting plate 703 is pushed toward the discharge conveyor 7 by means of a clearing mechanism 712. The clearing mechanism 712 includes a plurality of clearing bars 713, a first swing arm 714 for supporting the clearing bars 713, and a second swing arm 715 connected to the first swing arm 714. The connecting portion between the first and second swing arms is rotatable about an axis of a shaft 716. A free end of the second arm 715 is rotatably provided with a cam follower 717 which is in surface contact with a cam surface of a cam member 718 rotatable about an axis of the shaft 710.

The cam members 718 and 722 are coaxially rotatable about the identical axis of the shaft 710 to which a gear wheel $g_1$ is integrally provided. The gear wheel $g_1$ is in meshing engagement with a gear wheel $g_2$ which is rotated by a motor 719.

By the rotation of the motor 719, the discharge arm 701 of the upstanding mechanism 700 is rotatably movable between its horizontal and vertical positions because of the contact between the cam member 722 and the cam follower 711. When the discharge arm 701 is at vertical position shown by a broken line in FIG. 37, the containers are transferred from the discharge lifter 49 into the upstanding mechanism 700. Further, the clearing mechanism 712 is also operated in sequential timing relative to the operation of the upstanding mechanism 700. Therefore, upstanding containers 1 are moved into the discharge conveyor 7 by the clearing mechanism 712, when the discharge arm 701 is at its horizontal position shown by a solid line in FIG. 37.

Figure 38:
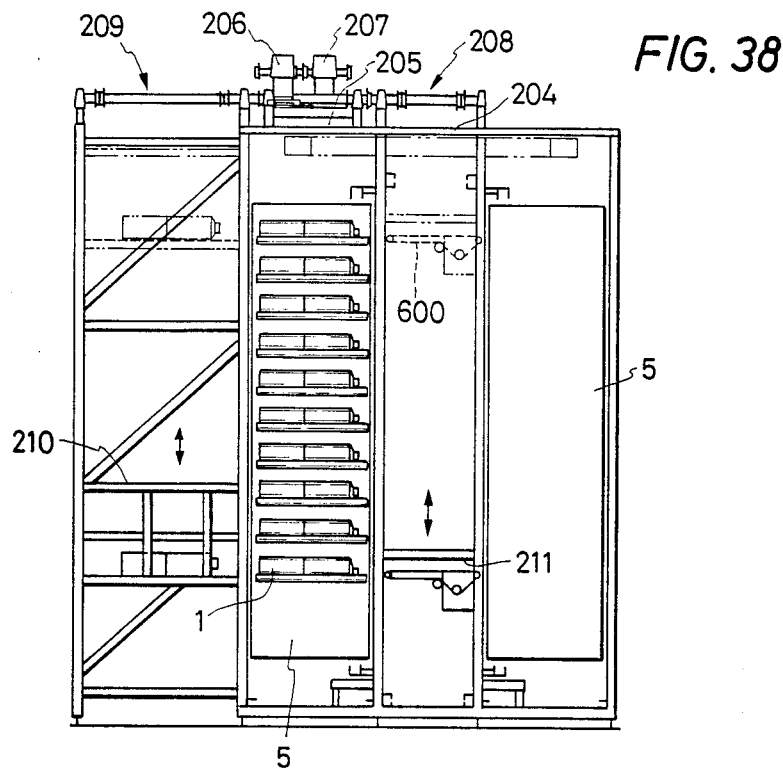
FIG. 38 is an elevational view as viewed from running direction of the racks and showing infeed and discharge stations according to a modified embodiment of this invention.

The infeed lifter 210 and the discharge lifter 211 are vertically movable by the acuations of the hydraulic motors etc. as described above. According to still another embodiment of the present invention shown in FIG. 38, a base plate 205 horizontally extends from an uppermost surface of the vertical frame plate 204 shown in FIG. 4, so that the base plate 205 is positioned above the culturing rack 5, and the motor 206 for driving the infeed lifter 211 and the motor 207 for driving the discharge lifter 211 are mounted on the base plate 205 in such a manner that these motors are spaced away from each other in directions parallel with and perpendicular to the travelling direction of the racks 5. The infeed and discharge lifters 210 and 211 are vertically movable by these motors 206 and 207 through power transmission mechanisms 208 and 209, respectively.

Handling Station

Figure 39:
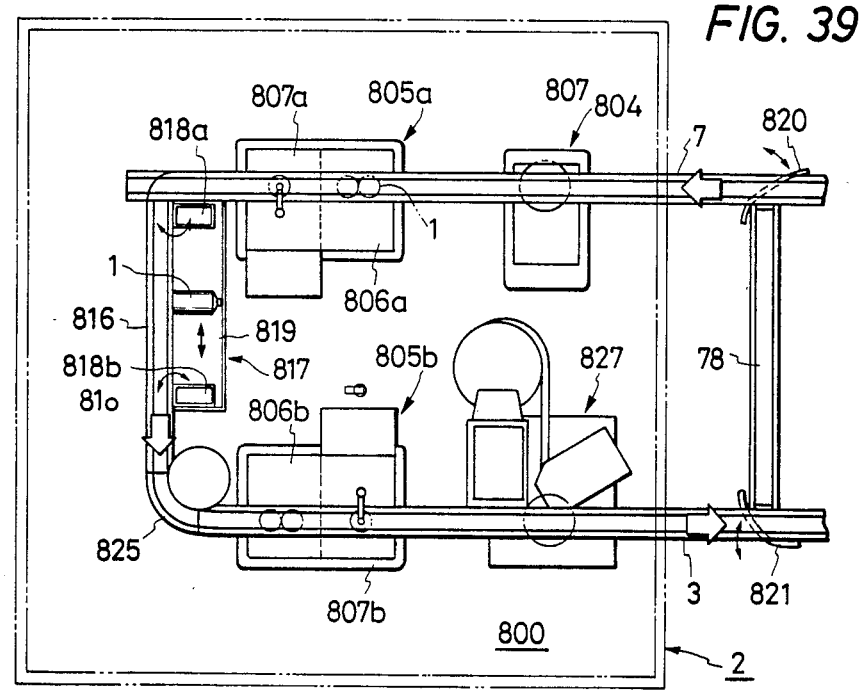
FIG. 39 is a plan view showing a container handling station.

The above described handling station for handling the culturing containers (hereinafter referred to as roller bottles) is shown in FIG. 39. In the handling station, a sterilized chamber 800 is provided, and the discharge conveyor 7 enters the chamber 800. Along the discharge conveyor 7 and within the chamber 800, disposed are a cap removing unit 804 for removing a cap 1a of the roller bottle 1, and a first liquid sucking and filling unit 805. The first liquid sucking and filling unit 805 includes a first liquid sucking portion 806a and a first liquid filling portion 807a, and is driven by a positive-displacement pump as a drive source such as reciprocating piston-cylinder, rotary-vane, gear or lobe mechanism.

A transferring conveyor 816 is disposed at a position adjacent to a distal end of the discharge conveyor 7 and is directed perpendicular thereto. Further, a bottle rolling unit 817 is juxtaposedly installed along the transferring conveyor 816 so as to fall down the upstanding bottles and provide rolling motion to the same. In the rolling unit 817, tiltable plates 818a and 818b are provided at both inlet and outlet portions thereof. The tiltable plates are swingable between their vertical and horizontal positions for falling down and upstanding the roller bottles 1. Between the tiltable plates 818a and 818b, a slant plate 819 is provided which is gradually inclined downward toward the travelling direction of the transferring conveyor 816 so as to permit the roller bottles fallen down to be rollingly displaced. The tiltable plate 818a receives the roller bottle 1 which is displaced from the transferring conveyor 816 by a pusher (not shown), and is gradually inclined toward its horizontal direction for lying the roller bottle 1. And the tiltable plate 818b is adapted to hold the bottle 1 rolling down along the slant plate 819 and to render the bottle to be moved to its upstanding position and be displaced onto the transferring conveyor 816. An outlet end of the transferring conveyor 816 is connected, through a guide plate 825, to an infeed conveyor 826 extending perpendicular to the transferring conveyor 816. The infeed conveyor 825 is provided with a second liquid sucking and filling unit 805b having the construction the same as the first liquid sucking and filling unit 805a described above. The second liquid sucking and filling unit 805b includes a second liquid sucking portion 806b and a second liquid filling portion 807b, and a positive-displacement pump is provided for driving the second unit 805b. At a downstream side of the second unit 805b, a cap fitting unit 827 for providing the cap to the roller bottle 1 is disposed.

In the handling station 2, the roller bottle 1 is selectively subjected to various treatment such as injection of the culture medium, cleaning, and sucking of the culture medium when the bottle 1 passes through the above mentioned units. Further, a bypass conveyor 78 is disposed at a position outside of the sterilized chamber 800. The bypass conveyor 78 extends in a direction perpendicular to the infeed and discharge conveyors 3 and 7. Guide plates 820 and 821 are disposed at both distal ends of the bypass conveyor 78. The guide plates 820 and 821 are selectively operated so as to displace the roller bottle 1 carried by the discharge conveyor 7 directly toward the infeed conveyor 3 obviating the insertion of the roller bottle 1 into the sterilized chamber 8.

Next, examples of cell culturing processes will be described with reference to FIG. 40.

Referring to a first step, new roller bottles 1 are juxtaposed on the discharge conveyor 7, and the conveyor 7 is driven. Caps of the roller bottles 1 on the conveyor 7 are removed by the opener 804, and the first cultured liquid is filled into the bottles by the first filling portion 807a. Thereafter, the roller bottles 1 are transferred, through the transferring conveyor 816, to the infeed conveyor 3 at which the roller bottles 1 are subjected to cell inoculation by the second filling portion 807a. Thereafter, the bottles are capped with caps at the cap fitting unit 827. Thus processed bottles 1 are transferred to the infeed station 4.

At the infeed station 4, the roller bottles are successively accommodated into the culturing rack. When two racks are completely filled with the bottles 1, succeeding two racks are brought to a position in front of the infeed station 4 for accomodating the bottles thereinto. Each of the roller bottles 1 is rotated about its axis by the rollers 41 within the rack for culturing for a predetermined period of time. Upon completion of the culturing, the racks are successively moved to a position in front of the discharge station 6, and bottles are taken out of the rack 5 and are positioned on the discharge conveyor 7.

Turning next to a second step, the caps of the roller bottles 1 transferred by the discharge conveyor 7 into the sterilized chamber 800 are removed by the cap removing unit 804, and liquid in the bottles 1 are removed by the first suction unit 806a. The bottles 1 are subjected to rinsing by injecting cleaning liquid into the bottles 1 by the first liquid filling portion 807a. Thereafter, the roller bottles 1 rollingly travel along the rolling unit 817 because of their gravity for rinsing the interior of the roller bottles. The rinsing liquid is removed by the second suction portion 806b and a new culture medium (second culture liquid) is filled by the second filling portion 807b. Then, the bottles 1 are capped with the caps at the second cap fitting unit 827. Thus treated roller bottles 1 are transferred to the infeed station 4 for the next culturing operation. Such roller bottles 1 are accommodated in the rack 5 by the infeed station 4, and the roller bottles 1 are recovered on the discharge conveyor 7 after completion of the predetermined cell culturing for a predetermined period of time.

Turning to a third step, the bottles 1 transferred into the sterilized chamber 800 are subjected to cap removing operation at the cap removing unit 804, and thereafter, the bottles 1 merely pass through the first liquid suction and filling portion 805a. At the second liquid suction and filling portions, 806b and 807b, the internal liquid is removed and new liquid culture medium (a third culture liquid) is filled in the bottle. Thereafter, the bottles 1 are capped with the caps at the cap fitting unit 827. Thus treated bottles 1 are transferred to the infeed station 4, and are subjected to culturing for a predetermined period of time in the rack 5. After the culturing, the bottles are removed from the rack 5 and are positioned on the discharge conveyor 7.

Turning to a fourth step, the bottles entered into the sterilized chamber 800 is subjected to cap removing by the cap removing 804, and then, a paste which serves as a forming liquid is collected by the first suction portion 806a. The bottles are then capped with the caps by the cap fitting unit 827. Therefore, overall steps are completed.

Next, operations in the cell culturing apparatus according to the present invention will be described.

Figure 41A:
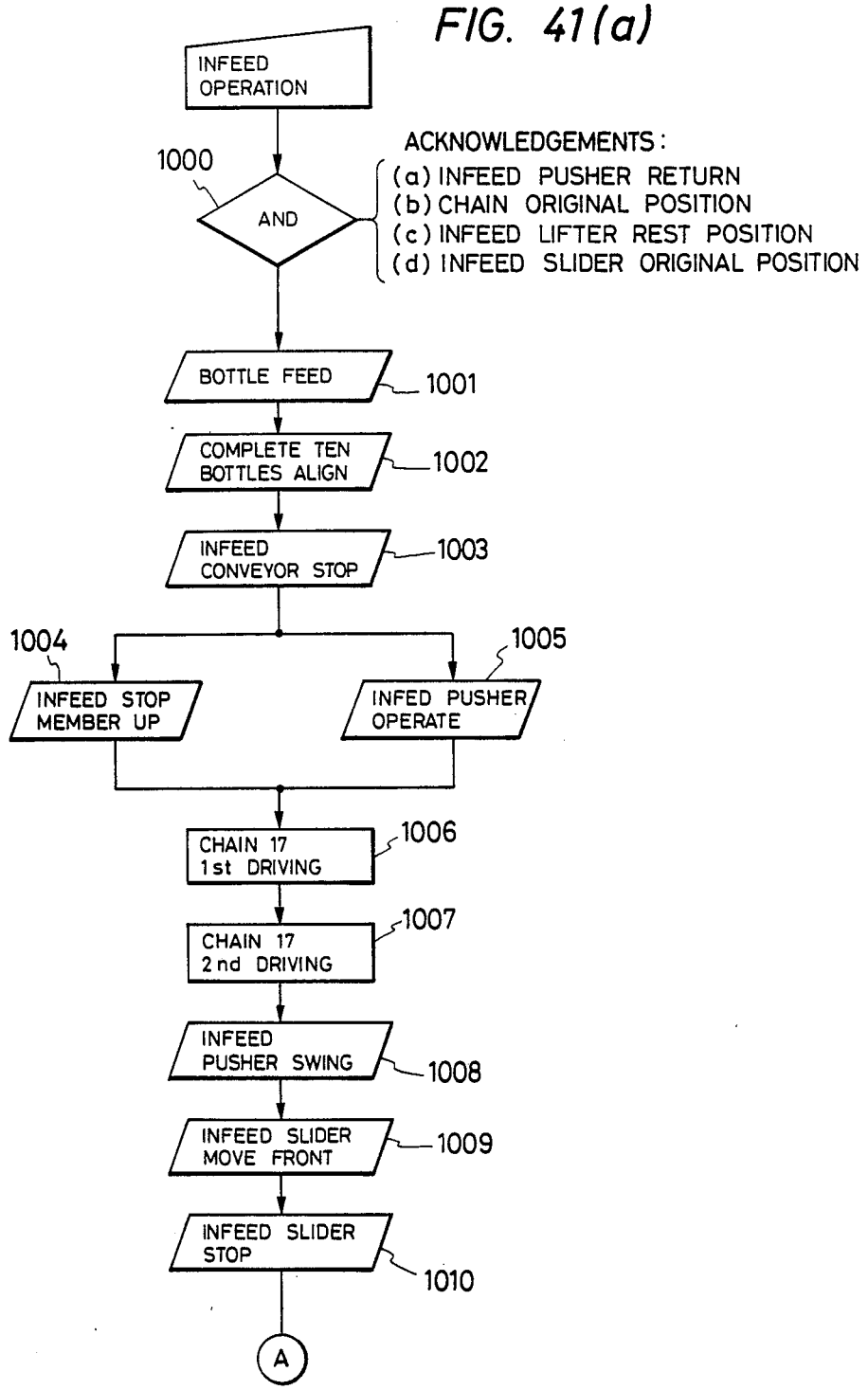
FIGS. 41 through 45 are flow-charts showing infeed operation mode, discharge operation mode, simulteneous infeed and discharge operation mode, inspection operation mode, and back-up operation mode, respectively.
Figure 41B:
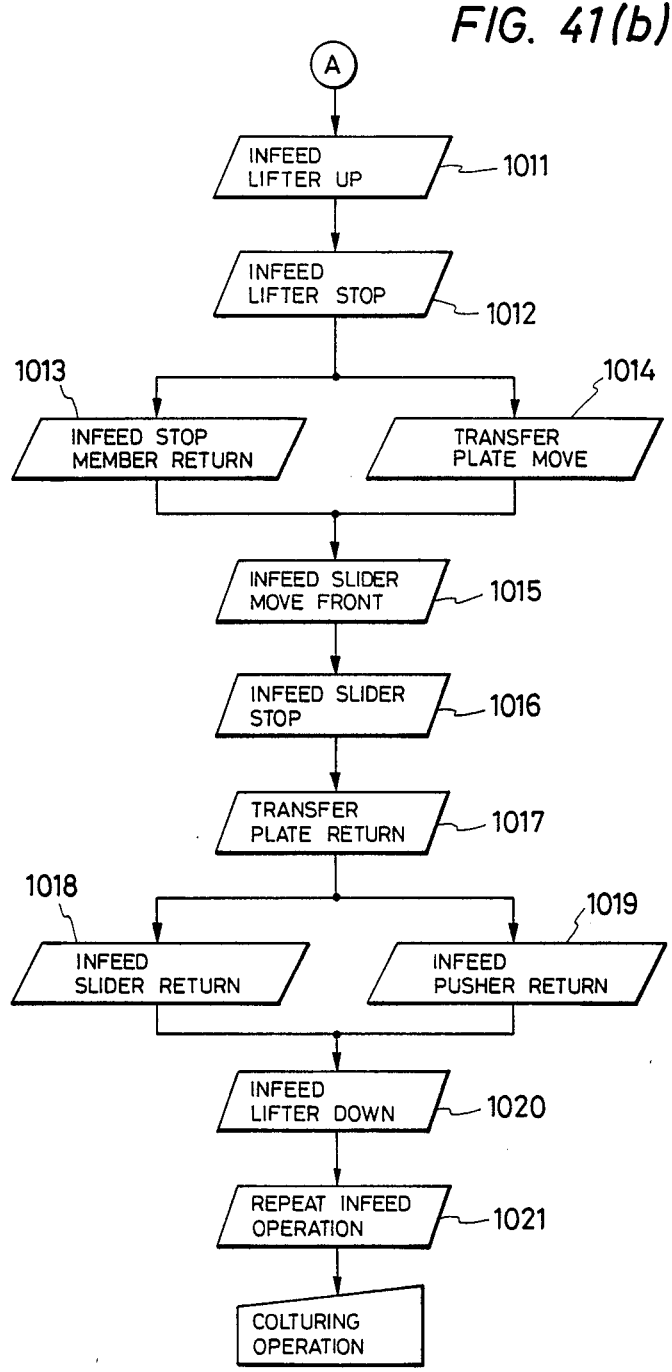

(1) Infeed Operation (FIG. 41)

According to the infeed operation, roller bottles containing fresh culture medium and cells are supplied into the rotary rack 5 of the rack supporting apparatus S. In FIG. 1, totally thirty-two culturing racks 5 are arranged in the loop path, and all racks 5 are subjected to accommodation of the roller bottles.

Firstly, in a step 1000, acknowledged are (a) a position of the infeed pusher 12 as shown in FIG. 8, (b) position of the chain 17 as shown in FIG. 8, (c) rest position (lowermost descent position) of the infeed lifter 10 as shown in FIG. 8, and (d) leftmost position of the infeed slider 23 as shown in FIG. 8, and then, infeed conveyor 2 is operated in step 1001. In step 1002, when the sensor 301 detects five roller bottles, the stop unit 302 is operated, and the second stop unit 304 is operated upon detection of tenth roller bottle. Thereafter, in step 1003, the infeed conveyor 3 is stopped, and infeed stop member 20 is moved to its ascent position simultaneously with the pushing operation of the infeed pusher 12 in steps 1004 and 1005. Thus, ten roller bottles are mounted on the dog 17a. In step 1006, the chain 17 is driven in a normal direction to transfer, along the arcuate guide member 16a, ten roller bottles arranged side by side toward the rear end of the guide member 16b of the infeed lifter 10. During this transferring state, operations from steps 1002 to 1003 are performed, so that the chain 17 is rotated by a single stroke to restore its original position, and operation according to the step 1005 is repeated. Then subsequent ten roller bottles are also transferred toward the rear end of the guide member 16b by another rotation of the chain 17 (step 1007). As a result, front ends of the subsequent ten roller bottles push the rear ends of the leading ten roller bottles already reached to the guide members 16b, and accordingly, the two roller bottles (front and rear bottles) are respectively mounted on each of the guide members 16b.

Then, the cylinder 29 is actuated to swing the infeed member 28 for positioning the bottles 1 at their initial position in step 1008. The motor 27 is energized to move the infeed slider 23 to its intermediate position where the front end of the front roller bottle abuts the stop member 20 protruding from the front end of the infeed lifter 10, and the motor 27 is deenergized in steps 1009 and 1010. Next, the infeed lifter 10 is elevated to a position corresponding to uppermost stage position of the rack 5, and the upward movement of the lifter 10 is stopped at that position in steps 1011 and 1012. Thereafter, the infeed stop member 20 is moved to its descent position for relaxing the front end of the front roller bottle 1 in a step 1013, and at the same time, the transferring plates 18 is moved in a frontward direction in step 1014. Then, the infeed slider 23 stopped at the intermediate position is again in a frontward direction, so that bottles are inserted into the uppermost stages of the two racks 5 juxtaposed with each other in step 1015. The movement of the slider 23 is stopped upon completion of the insertion in step 1016. Then, the transferring plate 18 is moved toward its original position in step 1017, and further, the infeed slider 23 is moved to its original position in step 1018 concurrent with the movement of the infeed member 28 toward its original position by the actuation of the cylinder 29 in step 1019. Then, the infeed lifter 10 is moved to its descent position in step 1020 to thus terminate the bottle infeed operation with respect to the single stage of the rack 5. The above described operations are repeatedly carried out for the remaining stages of the rack in step 1021. If the first two racks 5 are completely filled with the roller bottles 1, subsequent two racks 5 are moved to the bottle infeeding positions, and the above-described infeed operations are again performed. After each of the racks is completely filled with the roller bottles 1, culturing operation is initiated. That is, the drive motor 39 in each of the racks 5 is energized in order to rotate the rollers 41 for rotating the roller bottles 1 supported thereon.

Figure 42A:
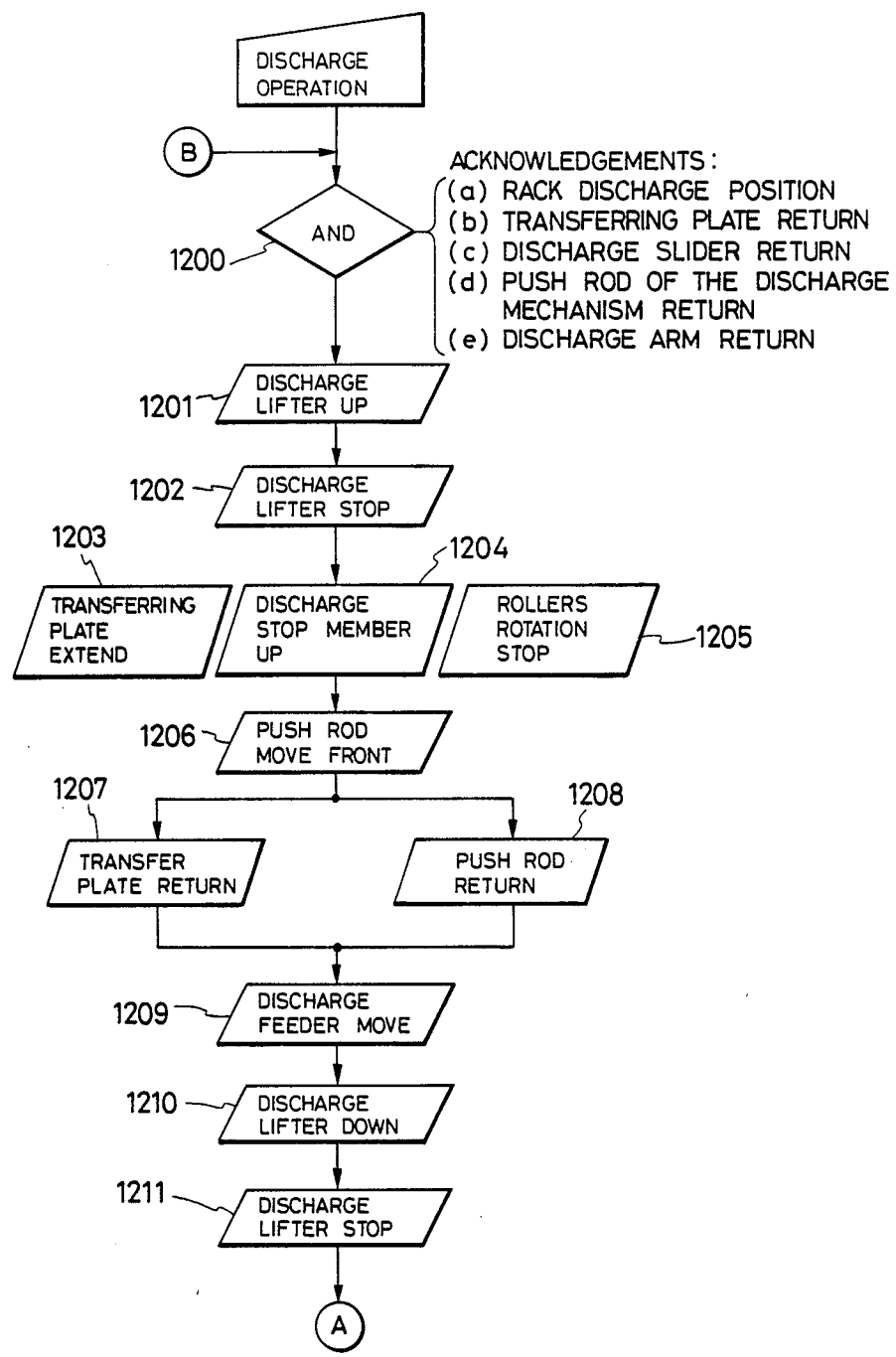
Figure 42B:
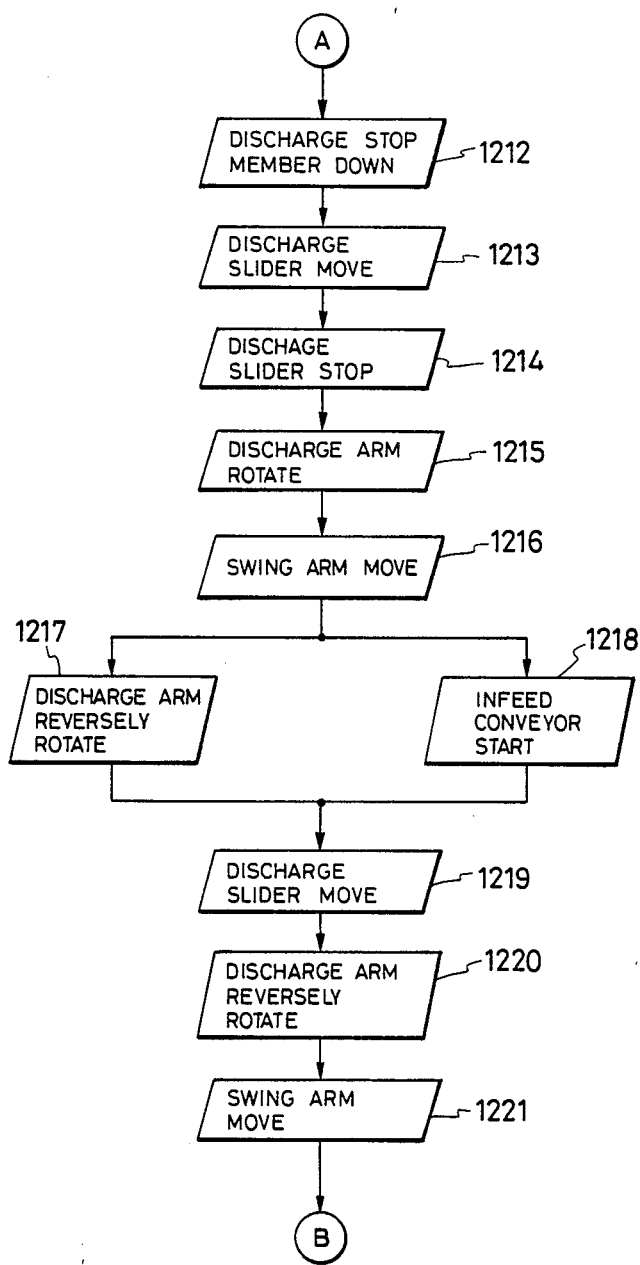

(2) Discharge Operation (FIG. 42)

In the discharge operation, roller bottles 1 in the culturing rack 5 are discharged therefrom. Such bottle discharge is required for the exchange of culture medium contained in the bottle with a fresh culture medium, or for collecting targetting material formed in the bottle by the cultivation therefrom.

In step 1200, acknowledged are (a) the suspended positions of the two racks 5 at their discharge positions, (b) restoration of the transferring plate 56 to its original position, (c) original position (frontward position) of the discharge slider 61, (d) original position of the push rod 55 of the discharge mechanism 48, and (e) bottle receiving position of the discharge arm 69 of the upstanding mechanism 51 as shown in FIG. 27. Then, the discharge lifter 49 is elevated and is stopped at a position corresponding to the uppermost stage of the two racks 5 in steps 1201 and 1202. Thereafter, the transferring plates 56 extend into the racks 5 in step 1203, the discharge stop member 58 is moved to its ascent position in step 1204, and the driving of the rollers 41 are suspended in step 1205. The push rod 55 is moved toward the culturing racks 5 in step 1206 for pushing the roller bottles 1 from the racks 5 onto the discharge lifter 49, and thereafter, the transferring plates 56 are restored to their original positions, while the push rod 55 is retracted in steps 1207 and 1208. Further, the cylinder 67 is operated to swing the discharge feeder 66, so that the front end of the front roller bottle 1 is held by the feeder 66 in step 1209, and the discharge lifter 49 is moved to its descent position and is stopped thereat in steps 1210 and 1211. Then, the discharge stop member 58 is moved to its descent position in step 1212 to allow the bottles to pass thereover, and the discharge slider 61 is moved to its intermediate position and is stopped in steps 1213 and 1214. In this case, the receptacle bars 68 of the upstanding mechanism 51 are at their bottle receiving positions, so that ten bottles arranged side by side are dropped onto the receptacle bars 68. Then, the discharge arm 69 is moved in counterclockwise direction in FIG. 27 in step 1215, and the swinging movement of the discharge arm 69 is stopped at horizontal orientation thereof. Then, the swing arm 74 is operated to displace the bottles on the support plate 69a toward the discharge conveyor 7 in step 1216. Next, the discharge arm 69 is reversely rotated in the clockwise direction in FIG. 27, and the discharge conveyor 7 is driven by a certain length and is stopped, so that the subsequent ten bottles can be shifted onto the conveyor 7 in steps 1217 and 1218. Further, the discharge slider 61 is moved from its intermediate position toward the upstanding mechanism 51 and is stopped in step 1219. In this case, the receptacle bars 68 of the discharge arm 69 receive thereon the front ten roller bottles 1, and the discharge arm 69 is rotated in counterclockwise direction in FIG. 27 to its horizontal orientation in step 1220, and then the swing arm 74 is operated to displace the ten roller bottles toward the discharge conveyor 7 in step 1221. Thereafter, the discharge arm 69 and the discharge slider 69 are moved back to its original position for the next bottle receiving operation. Such sequential operations are repeatedly carried out in accordance with every stage of the culturing rack 5, and therefore, all roller bottles 1 are discharged from all stages of the rack 5. After the discharges of the bottles from the two racks are completed, subsequent two racks are moved to the bottle discharge positions, and above-described discharge operations are repeatedly carried out.

Figure 43:
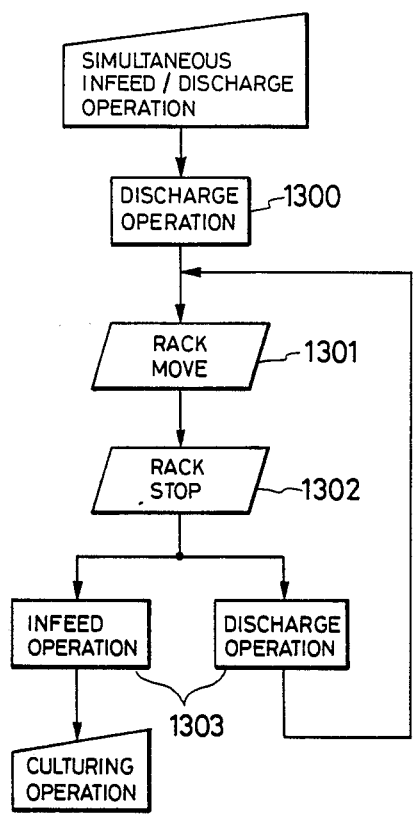

(3) Simultaneous Infeed and Discharge Operations (FIG. 43)

In the simultaneous operations, exchanged is culture medium in the roller bottle which is subjected to culturing for a predetermined period of time. That is, after the cultivation for the predetermined period, nutritive substance in the culture medium is decreased, while metabolic substance such as ammonia and lactic acid etc. is increased in the culture medium. Therefore, metabolic substance containing medium is required to be replaced by the fresh culture medium. For the exchange of the culture medium, the discharged roller bottles 1 are subjected to treatment at the handling station 2, and are again returned into the culturing rack 5.

In FIG. 43, at the bottle discharge position, roller bottle discharge operations with respect to the first two racks are conducted in step 1300. After the two racks are subjected to complete bottle removal, the racks are moved by a length equal to the two racks in running direction thereof, so that subsequent two racks are brought into the bottle discharge positions in step 1301 for the bottle discharge operations. The roller bottles discharged from the racks 5 are transferred into the handling station 2 for the above-described exchanging operation, and are transferred to the infeed station 4 through the infeed conveyor 3. When the two empty racks are brought to the bottle infeed positions, roller bottles treated at the handling station 2 are supplied into the two racks 5 in step 1302. During these operations, the bottle discharge operations are continuously performed in accordance with step 1303. Therefore, roller bottles fed into the racks are subjected to the culturing operation.

Figure 44:
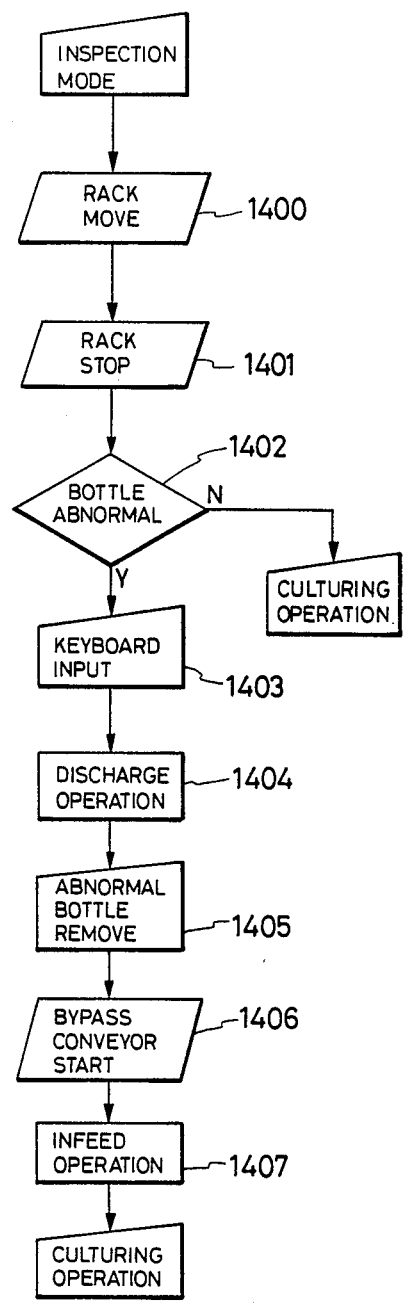

(4) Inspection Operation (FIG. 44)

The inspection operation is required to prevent roller bottles from infectious contamination with microorganism, when one of the roller bottles is contaminated with microorganism by provisionally inspecting the color change of the roller bottles.

For the inspection, personnel is stationed on a predetermined inspecting spot 47 shown in FIG. 1, and visual observation to the color change of the roller bottles is conducted by automatically moving and temporarily stopping the racks in front of the personnel in steps 1400, 1401 and 1402. If an abnormal bottle is found, a rack number and a stage number which houses and installs the abnormal bottle is inputted through a numerical key of an operation key board in step 1403. The bottles at the stored stage of the stored rack are all discharged into the discharge conveyor 7 when the rack stored through the key board is brought to the bottle discharge position in step 1404. Among the discharged bottles, normal bottles are also inclusive, and therefore, the abnormal bottle is selected in step 1405, and the bypass conveyor 78 is operated in step 1406 to carry remaining normal bottles to the infeed conveyor 3. In this instance, the specific rack is moved to the bottle infeed position, so that the normal bottles carried by the infeed conveyor 3 are again supplied into the rack for continuing culturing operation in steps 1407 and 1408.

(5) Back-up Operation

Cell cultivation is continuously carried out day and night. If one of the drive rollers 41 is damaged to stop its rotation due to a sudden trouble, rotations of the roller bottles are not carried out. If such hindrance has not been found for a long period, cells in the bottles may die, and great deal of damage will be done to the cell cultivation. Nonetheless it would be almost impossible for personnel to visually insepect the cell cultivation, day and night. In light of the above, the back-up mode operation takes a safe measure to the accidental cell culturing, in which the above described trouble is electrically detected, and roller bottles at the abnormal rack are replaced onto a normally operated auxiliary rack immediately after the discovery of the abnormalities.

In the cell culturing apparatus according to the present invention, bottle infeed and discharge operations are made with respect to the two confronting racks. However, such bottle infeed and discharge can be made with respect to one single rack.

In the back-up operation, total travel lengths of the infeed conveyor 3, the bypass conveyor 78 and the discharge conveyor 7 should be longer than the length given by the sum of outer diameters of the roller bottles which are discharged from the abnormal rack so as to afford to receive the discharged roller bottles upstandingly arranged side by side on these conveyors. Further, as least one auxiliary rack is supplementally disposed on the rack supporting apparatus S. Moreover, the numbers of the racks can be changeable by changing the position of the drive sprocket 36 shown of FIG. 2.

Figure 45:
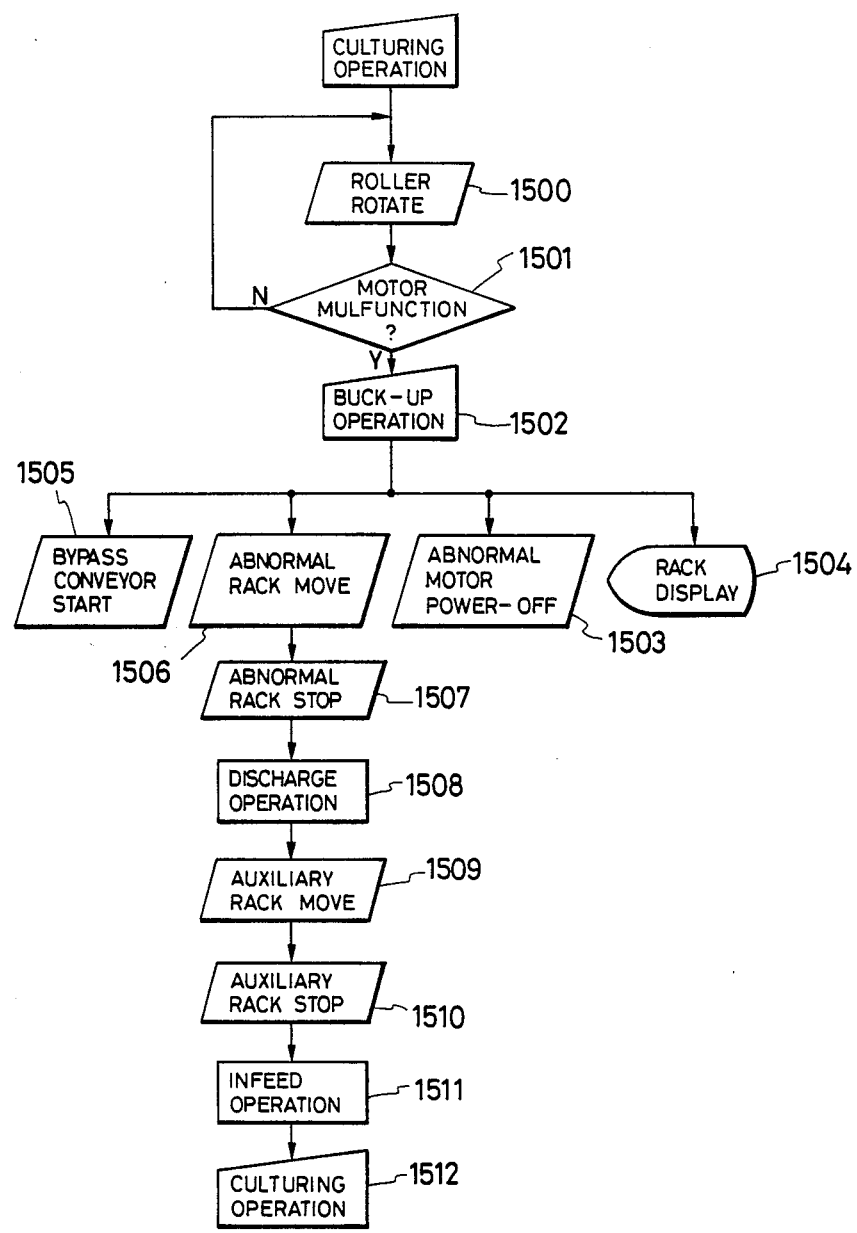

In FIG. 45, during the culturing operation, the drive motor 38 in the culturing rack 5 is operated in step 1500. If the motor 38 becomes in inoperable condition as shown in step 1501, back-up operation is initiated as shown in step 1502. Electrical power supply to the rack housing the abnormal motor is shut-off in step 1503, and the rack number housing the abnormal motor is displayed in step 1504. At the same time, the bypass conveyor 78 is operated in step 1505, so that the abnormal rack is displaced to the bottle discharge position and is stopped thereat in steps 1506 and 1507. At the bottle discharge position, all roller bottles accommodates in the abnormal rack are discharged thereform in step 1508, and the emplty auxilliary rack is shifted to the bottle infeed position and is stopped thereat in steps 1509 and 1510. The all roller bottles discharged at the discharge position are travelled through the bypass conveyor 78 and are reached to the infeed position without passing through the handling station 2, so that all roller bottles are accommodated in the auxiliary rack stopping at the infeed position, and the culturing operation is restarted in steps 1511 and 1512.

According to the foregoing embodiments, automatically inserted into the culturing racks are the culturing containers (roller bottles) which are subjected to automatic filling of the culture medium and cells at the handling station, and the cells cultured in the containers at the culturing racks are automatically discharged therefrom and the containers are automatically returned back to the handling station. Therefore, complete automatic filling of the cell and the culture medium, culturing, and exchange of the culture medium are attainable.

Further, the culturing racks are displaceable on the loop track, and therefore, such movable arrangement can facilitate inspection to the culturing container in the racks. Moreover, even if there is abnormality in one or another of the culturing container during culturing, abnormality is promptly detected, and the containers in the abnormal rack are replaced easily into other normally operable culturing rack for continuing the cultivation because of the back-up function of this invention. Furhter, the number of the culturing racks are changeable and the rotary loop length is also changeable in accordance with the numbers of the racks. Thus, cell cultivation capacity is also controllable in the present invention.

In the above-described embodiments, fully automatic operations are attained by the infeed and discharge stations 4 and 6. However, semi-automatic cell culturing system is also conceivable by the introduction of manual operator's labour.

Figures 40, 47:
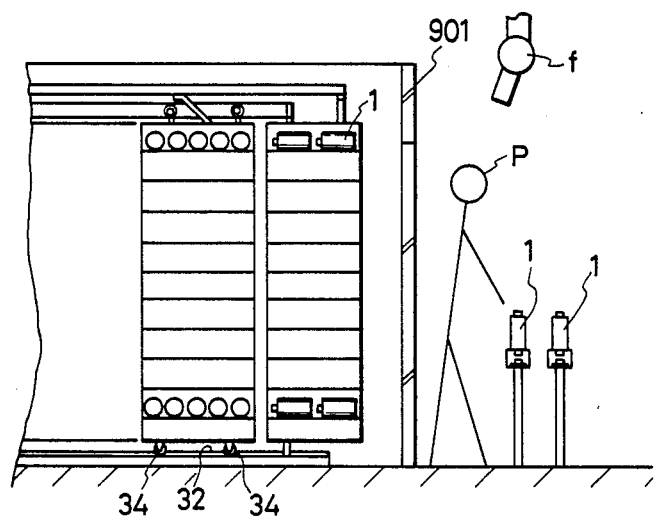
FIG. 40 is a operational diagram in the container handling station.

In FIGS. 46 and 47, the semi-automatic culturing system 900 is provided with a culturing chamber 901. At right side wall of the chamber 901 in the Figure, there are provide a plurality of handling windows 902, and a door 903 is provided, so that the operator can have access to the culturing chamber 901. The above-described rotary type rack supporting apparatus S is juxtaposedly installed in the culturing chamber 901.

On the other hand, culturing container handling apparatus 905 is disposed at a position confronting the side wall at which the windows 902 are provided. In the handling apparatus 905, conducted are supply of the culture medium, cell inoculation, and rinsing with respect to the culturing containers. A working space 907 is provided between the culturing chamber 901 and the handling apparatus 905 for the purpose of operators' labour. Along the working space, discharge and infeed conveyors 906a and 906b of a conveying means 906 are installed.

In the handling apparatus 905, there are provided a cap removing unit 903 for removing the caps of the roller bottles 1, a first suction portion 909 for sucking liquid in the roller bottles, and a first filling portion 910 to inject culture medium into the bottles for the inoculation of cells. Betweend an outlet end of the discharge conveyor 906a and an inlet end of the infeed conveyor 906b, a transferring conveyor 912 is installed. Alongside the transferring conveyor 912, a bottle rolling unit 911 is disposed to rollingly move the roller bottles thereon toward the inlet end of the infeed conveyor 906b. Further, along the infeed conveyor 906b, there are provided a second suction portion 913 for sucking liquid in the bottles, and a second filling portion 914 for injecting culturing liquid into the bottles. Furthermore, a cap fitting unit 915 is disposed for providing caps onto the bottles at a downstream side of the second filling portion 914.

These units and segments in the semi-automatic system provide the functions the same as those attendant to the corresponding units and segments in the full-automatic system. Operators P stand on places adjacent to the handling windows 902 and manually perform bottle infeed and discharge operations between the chamber 901 and the handling apparatus 905. A control box 916 is provided for each of the operators. The operator manipulate the control box 916 for driving the conveyors and for operating the actuation or deenergization of the rack supporting apparatus S. A rotary fan f is disposed above each of the operators p for blowing purified air toward the operators (FIG. 47).

According to the semi-automatic culturing system, operators' working positions are defined between the culturing chamber 901 and the handling apparatus 905, and the working area is outside of the culturing chamber 901. Therefore, efficient working is attainable and comfortable working circumstance is provided for the operator in order to handle the culturing containers without suffering from high temperature such as about 37° C. which temperature is provided within the culturing chamber 901.

What is claimed is:

1. A cell culturing apparatus comprising:
  a culturing chamber having side walls defining an internal space;
  means for maintaining said internal space at a predetermined temperature;
  handling windows provided at one side wall of said culturing chamber;
  at least one rotary rack supporting apparatus installed in said culturing chamber, said rack supporting apparatus comprising a loop track and a plurality of culturing racks adapted to travel on said loop track, said culturing racks accomodating therein a plurality of culturing containers;
  container handling stations disposed adjacent to said one side wall of said culturing chamber having means for filling culture medium into said culturing containers, cell inoculation thereinto, and rinsing said culturing containers;
  a working spot provided between said one side wall and said container handling stations having means for removing said culturing containers from said culturing rack through said handling windows to feed the containers into said container handling apparatus and for transferring said culturing containers from said container handling apparatus to said culturing rack; and, a transferring conveyor means having a part installed on said working spot and a remaining part installed on said container handling station for feeding the culturing containers from said working spot into said container handling apparatus and vice versa.

2. A cell culturing apparatus which uses culturing containers containing therein cells and culture medium for cell culturing, comprising:

a rack supporting apparatus comprising a loop tracking means and a plurality of culturing racks each connected one after another in series and adapted to travel on said loop tracking means, each of said racks accommodating therein said culturing containers for cell culturing;

an infeed station disposed at a position alongside said loop tracking means for automatically supplying said culturing containers into said culturing racks, said infeed station comprising an infeed lifter which is vertically movable for temporarily mounting thereon said culturing containers in order to supply the culturing containers into said culturing racks and a position changing mechanism for rotating said culturing containers from an upstanding position by about 90° into a horizontal position to transfer the culturing containers to said infeed lifter in said horizontal position; and a discharge station disposed at a position alongside said loop tracking means for automatically discharging said culturing containers which have been subjected to culturing from said culturing racks, said discharge station comprising a discharge lifter which is vertically movable for temporarily mounting thereon said culturing containers in order to discharge the culturing containers from said culturing racks and an upstanding mechanism disposed adjacent said discharge lifter for, after travel of said containers through said discharge lifter, upstanding said culturing containers which have been lying in said horizontal position in said culturing racks.

3. The cell culturing apparatus as defined in claim 2, wherein said discharge station further comprises a clearing mechanism for pushing culturing containers on said discharge lifter toward said upstanding mechanism of said discharge station.

4. The cell culturing apparatus as defined in claim 2, wherein said upstanding mechanism of said discharge station comprises: a discharge arm swingably providing its vertical orientation at which horizontally oriented culturing containers are received from said discharge lifter, and providing its horizontal orientation for transferring said containers onto said discharge conveyor;

receptacle bars extending from a tip end of said discharge arm in a direction perpendicular thereto for supporting peripheral surface walls of said culturing containers;

a support plate provided at said tip end of said discharge arm for supporting bottoms of said culturing containers;

a discharge arm drive mechanism for reciprocally swinging said discharge arm between said vertical and horizontal positions; and a clearing unit for transferring upstanding containers on said bottom supporting plate toward said discharge conveyor.

5. The cell culturing apparatus as defined in claim 2, wherein said discharge station further comprises a discharge mechanism disposed at a position opposite said discharge lifter with respect to said culturing rack for pushing said culturing containers in said rack toward said discharge lifter, said discharge mechanism being vertically movable along said culturing rack and having a pushing unit for pushing said culturing containers out of said rack.

6. The cell culturing apparatus as defined in claim 2, wherein said position changing mechanism comprises:

arcuate guide members having lower ends positioned in the vicinity of said infeed coveyor and upper ends directed toward said infeed lifted;

a chain disposed along said arcuate guide members, said chain integrally providing a support member; and an infeed pusher for pushing predetermined numbers of said culturing containers carried on said infeed conveyor toward said guide members, said support member carrying said containers pushed by said infeed pusher and moving said containers along said guide members while gradually inclining said containers toward hoizontal.

7. The cell culturing apparatus as defined in claim 6, wherein neighbouring guide members define a container guiding locus therebetween, said guide locus having a width gradually increased from said lower end toward said upper end of said guide members.

8. The cell culturing apparatus as defined in claim 2, wherein said position changing mechanism comprises;

arcuate guide members having lower ends positioned in the vicinity of said infeed conveyor and upper ends directed toward said infeed lifter;

an infeed pusher for pushing predetermined numbers of said culturing containers carried on said infeed conveyor toward said guide members;

a container infeeding unit adpated to move said culturing containers along said arcuate guide members for rotating said culturing containers by 90° from upstanding position to horizontal position, said container infeeding unit comprising: a supporting plate positioned outside said arcuate guide members for supporting bottoms of said culturing containers; support arms supporting said supporting plate and swingably movable between their horizontal and vertical positions; said containers supported on said supporting plate being gradually inclined toward horizontal during their travel on said guide members by upward swinging movement of said support arms, and a crank-drive mechanism connected to said support arms for reciprocally moveing said support arms; and, a container supporting unit for supporting a row of containers on said infeed conveyor, comprising: a container row supporting plate for regulating a row of said containers on said infeed conveyor and preventing said containers from dropping from said infeed conveyor; and a drive-cylinder for vertically moving said row supporting plate; said container row supporting plate being disposed between a lower end portion of said guide members and said infeed conveyor, said container row supporting plate being at its ascent position when said row of containers are brought to positions facing said acruate guide members, and being at its descent position when said infeed pusher pushes said row of containers toward said arcuate guide members.

9. The cell culturing apparatus as defined in claim 8, wherein neighboring guide members define a container guiding locus therebetween, said guide locus having a width gradually increased from said lower end toward said upper end of said guide members.

10. The cell culturing apparatus as defined in claim 2, wherein said infeed lifter is slidably provided with a first group of transferring plates extendable into said culturing rack when said culturing containers are inserted thereinto, and wherein said discharge lifter slidably disposes a second group of transferring plates extendable into said culturing rack when said culturing containers are discharged therefrom, said culturing containers being slidably movable on said transferring plates during said container insertion and container discharge with respect to said rack.

11. The cell culturing apparatus as defined in claim 10, wherein each of said transferring plates has a tapered tip portion so as to gradually reduce its height toward its tip end.

12. The cell culturing apparatus as defined in claim 2, further comprising:

a handling station for automatically filling said cells and said culture medium into said culturing containers and for automatically exchanging said culture medium in said culturing container for fresh culture medium;

an infeed conveyor disposed between said handling station and said infeed station; and, a discharge conveyor disposed between said handling station and said discharge station.

13. The cell culturing apparatus as defined in claim 12, further comprising a bypass conveyor disposed at a position adjacent to said hangling station, and between said infeed and discharge conveyors, said culturing containers discharged from said culturing racks being transferred from said discharge conveyor to said infeed conveyor through said bypass conveyor without passing through said handling station.

14. The cell culturing apparatus as defined in claim 13, wherein each of said culturing racks has a rotary mechanism for rotating said culturing containers about their axes, said culturing containers being transferred about their axes, said culturing containers being transferred into said racks in their horizontal orientation, and supported in said racks in horizontal position.

* * * * *